(12) United States Patent
Kularatne et al.

(10) Patent No.: US 10,786,580 B2
(45) Date of Patent: Sep. 29, 2020

(54) CHOLECYSTOKININ 2 RECEPTOR TARGETED NIR IMAGING AND USE THEREOF

(71) Applicant: On Target Laboratories, LLC, West Lafayette, IN (US)

(72) Inventors: Sumith A. Kularatne, West Lafayette, IN (US); Pravin Gagare, West Lafayette, IN (US); Mohammad Noshi, West Lafayette, IN (US)

(73) Assignee: On Target Laboratories, LLC, West Lafayette, IN (US)

( * ) Notice: Subject to any disclaimer, the term of this patent is extended or adjusted under 35 U.S.C. 154(b) by 0 days.

(21) Appl. No.: 15/699,272

(22) Filed: Sep. 8, 2017

(65) Prior Publication Data

US 2018/0071408 A1    Mar. 15, 2018

Related U.S. Application Data

(60) Provisional application No. 62/385,338, filed on Sep. 9, 2016.

(51) Int. Cl.

| | |
|---|---|
| *A61K 49/00* | (2006.01) |
| *C07K 5/02* | (2006.01) |
| *A61K 31/5513* | (2006.01) |
| *A61B 5/00* | (2006.01) |
| *A61K 45/06* | (2006.01) |
| *C07K 5/078* | (2006.01) |
| *A61K 47/64* | (2017.01) |
| *C07K 5/062* | (2006.01) |
| *C07K 5/065* | (2006.01) |
| *A61K 38/06* | (2006.01) |
| *C07D 401/14* | (2006.01) |

(52) U.S. Cl.
CPC ........ *A61K 49/0056* (2013.01); *A61B 5/0071* (2013.01); *A61K 31/5513* (2013.01); *A61K 38/06* (2013.01); *A61K 45/06* (2013.01); *A61K 47/64* (2017.08); *A61K 49/0032* (2013.01); *A61K 49/0052* (2013.01); *C07D 401/14* (2013.01); *C07K 5/0212* (2013.01); *C07K 5/0215* (2013.01); *C07K 5/0217* (2013.01); *C07K 5/06043* (2013.01); *C07K 5/06078* (2013.01); *C07K 5/06147* (2013.01); *A61B 5/6852* (2013.01); *A61B 2503/40* (2013.01); *A61B 2503/42* (2013.01)

(58) Field of Classification Search
CPC ....... A61K 49/00; A61K 31/5513; C07K 5/02
See application file for complete search history.

(56) References Cited

U.S. PATENT DOCUMENTS

| | | | |
|---|---|---|---|
| 4,331,646 A | 5/1982 | Delaage | |
| 5,962,451 A * | 10/1999 | Ryder | C07D 243/24 514/221 |
| 2005/0042283 A1 | 2/2005 | Wang | |
| 2013/0280281 A1* | 10/2013 | Castaigne | C07K 7/083 424/179.1 |
| 2014/0271482 A1* | 9/2014 | Low | A61K 49/0052 424/9.6 |
| 2015/0050212 A1* | 2/2015 | Low | C07D 405/12 424/1.69 |

OTHER PUBLICATIONS

PCT, International Search Report and Written Opinion Application No. PCT/US2017/050637, dated Nov. 3, 2017.
Korner, M. et al., CCK2 receptor splice variant with intron 4 retention in human gastrointestinal and lung tumours, Journal of Cellular and Molecular Medicine 14(4), pp. 933-943, 2010; p. 933, col. 1, paragraph 1-col. 2, paragraph 1.

* cited by examiner

*Primary Examiner* — Michael G. Hartley
*Assistant Examiner* — Jagadishwar R Samala
(74) *Attorney, Agent, or Firm* — McAndrews, Held & Malloy, Ltd.

(57) ABSTRACT

Compounds are described herein where CCK2R targeting ligands are attached to an imaging agent through a linker. The compounds can be used in the detection, diagnosis, imaging and treatment of cancer.

14 Claims, 29 Drawing Sheets

CHOLECYSTOKININ 2 RECEPTOR TARGETED NIR IMAGING AND USE THEREOF

RELATED APPLICATIONS

The present patent application claims the priority benefit of U.S. Provisional Patent Application No. 62/385,338, filed Sep. 9, 2016. The content of the aforementioned application is hereby incorporated by reference in its entirety into this disclosure.

TECHNICAL FIELD

The invention relates to methods of detecting, diagnosing, imaging and treating cancer in a subject.

BACKGROUND OF INVENTION

The cholecystokinin B receptor (also known as CCK2R, CCKBR, and the gastrin receptor) is a trans-membrane, G protein-coupled receptor. CCK2R is primarily expressed in (i) the brain and central nervous system, and (ii) the mucosa of the gastrointestinal tract, including parietal and ECL cells. It is reported to be most abundantly expressed in the cerebral cortex of the mammalian brain where it has been implicated in the regulation of memory/learning and response to stress. In the alimentary canal, its presence has been detected in the GI tissues, as well as exocrine and endocrine pancreas. Conflicting reports suggest the receptor is also expressed in peripheral tissues such as adipocytes, along with CCK1R, a G protein-coupled receptor with 50% homology to CCK2R. The natural ligands of CCK2R are gastrin and cholecystokinin peptides.

A number of different types of human tumors have been found that overexpress or ectopically express CCK2R in high densities or at high frequencies including medullary thyroid cancers, insulinomas, small cell lung cancers, bronchial, and ileal carcinoids, GIST tumors, and colon cancers, hepatocellular carcinomas, and pancreatic cancers. One manner in which disregulation of CCK2R signaling may contribute to tumor formation or growth relates to gastrin signaling through the receptor. Gastrin is a peptide hormone that stimulates secretion of gastric acid (HCl) by the parietal cells of the stomach upon binding of CCK2R. Gastrin has been reported to be an inhibitor of cancer cell apoptosis, likely through its ability to induce activation of the serine/threonine protein kinase PKB/Akt.[10] Several reports have shown that inhibiting the CCK2R receptor and the gastrin autocrine loop induces apoptosis and inhibits the proliferation of the cancer cell lines in vivo.

CCK2 receptors found in tumor tissue have been reported to include both normal protein as well as a constitutively active a CCK2R-receptor splice variant (CCK2i4svR) that has the fourth intron inappropriately retained, resulting in the addition of 69 amino acids in the third intracellular loop domain of the receptor, the domain known to be important for signal transduction.

Cytotoxic agents that target CCK2R might serve to block uncontrolled activation of the receptor in tumors. Helpfully, because CCK2R is expressed in normal brain tissue, the blood brain barrier will block polar compounds that could affect normal activity of the receptor in the brain. Therefore, where CCK2R and its splice variant are expressed outside of the brain by a tumor, the tumor will be the only tissue targeted by CCK2R and CCK2i4svR-specific cytotoxic agents.

CCK2R-specific antagonists have been developed and extensive structure-activity relationships have reported. Both in vitro and in vivo studies have demonstrated that the growth potentiating effects of gastrin can be abolished in the presence of selective CCK2R antagonists. One such antagonist is Z-360, an orally-active CCK2R antagonist (Zeria Pharmaceuticals Co., Ltd., Tokyo, Japan) that has a $K_i$=0.47 nmol/L with a selectivity ratio over CCK1R=672. Preclinical studies have shown that oral administration of Z-360 along with the chemotherapeutic gemcitabine significantly inhibited subcutaneous PANC-1 tumor growth compared with either agent alone (27.1% inhibition) and significantly increased survival compared with the vehicle. This antagonist is currently in Phase II human clinical trials for treatment of pancreatic cancer in combination therapy with gemcitabine.

The development of additional agents that selectively target CCK2R would broaden the arsenal of therapeutics that could be used in the treatment of tumors in which CCK2R is expressed. Such agents may also be used in the diagnosis and imaging of cancer in a subject.

BRIEF SUMMARY OF INVENTION

The present invention relates to a small group of highly related ligands that selectively target and bind CCK2R and the splice variant CCK2i4svR. The ligands are linked to NIR imaging agents, and these compounds are used in the treatment, diagnosis and imaging of tumors expressing CCK2R and the splice variant CCK2i4svR.

The invention is thus directed to compounds comprising a targeting ligand linked to an active moiety. The targeting ligand is compound that selectively binds to CCK2R and/or CCK2i4svR. The active moiety is a NIR imaging agent. The targeting ligand and the active moiety are joined by a linker as described herein.

In certain embodiments, compounds of the present invention have the form: B-L-Z wherein B is a CCK2R and/or CCK2i4svR-targeting molecule;

L is a spacer; and

Z is a NIR dye.

In some embodiments, the CCK2R and/or CCK2i4svR-targeted molecule is chosen from the group consisting of a small molecule, a ligand, an inhibitor, an agonist or a derivative thereof. In some embodiments, the CCK2R and/or CCK2i4svR-targeted compound is a ligand. In some embodiments, the CCK2-targeted compound is:

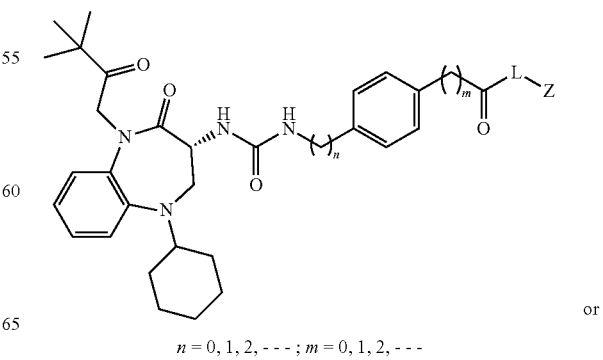

$n = 0, 1, 2, \text{---}; m = 0, 1, 2, \text{---}$ or

-continued

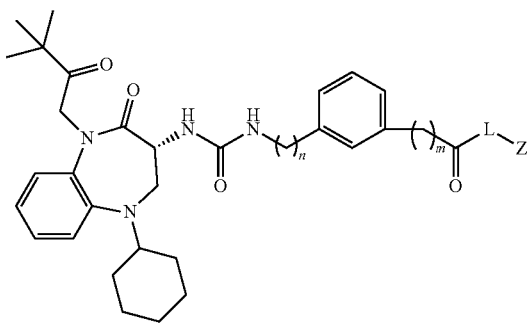

n = 0, 1, 2, - - -; m = 0, 1, 2, - - -

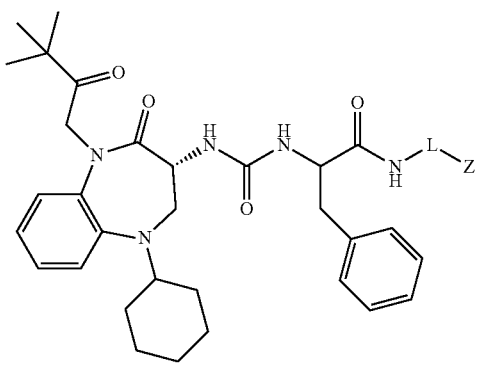

Or

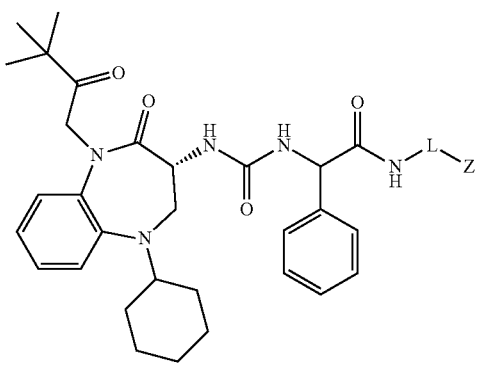

or

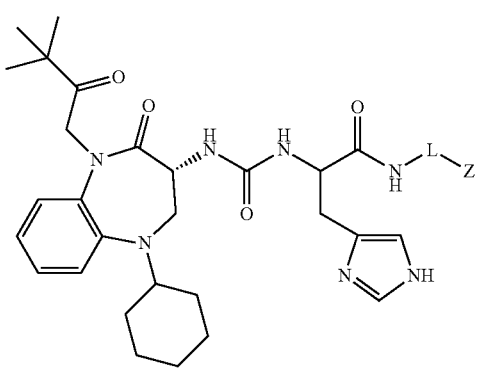

Or

-continued

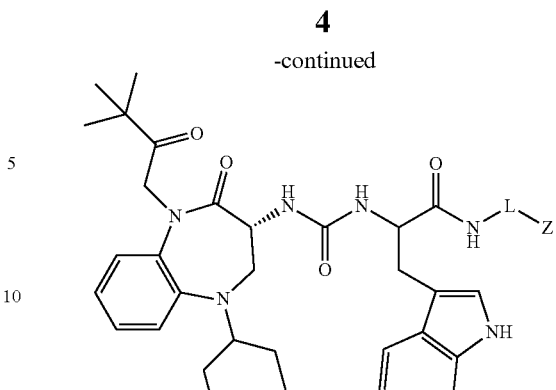

or

In some embodiments, L is selected from the group consisting of: acidic (negatively charged) amino acids, such as aspartic acid and glutamic acid and derivative thereof; basic (positively charged) amino acids such as arginine, histidine, and lysine and derivative thereof. In some embodiments, Y has a positive charge. In other embodiments, Y has a negative charge. In other embodiments, Y has a glutamic acid.

In some embodiments, Z is selected from the group consisting of near-infra red dyes, including but not limited to, IR800, Alexa Flour 647, SP0169, SP0189, or SP0196. SP196 shown as a species of:

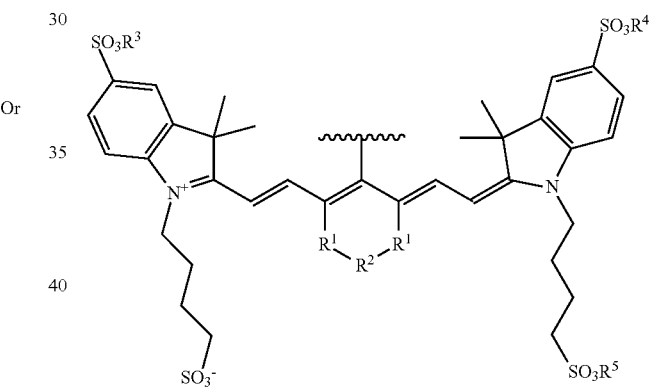

wherein, $R^1$ is independently selected from the group consisting of O, S, N, $CH_2$ and C, $R^2$ is independently selected from the group consisting of $CH_2$ and $CH_2CH_2$, and each of $R^3$, $R^4$, and $R^5$ are independently selected from the group consisting of H, Na, K, and $NH_4$. SP196 includes where R1, and R2 are each $CH_2$ and each of $R^3$, $R^4$, and $R^5$ are H.

In some embodiments, the CCK2-targeted compound is:

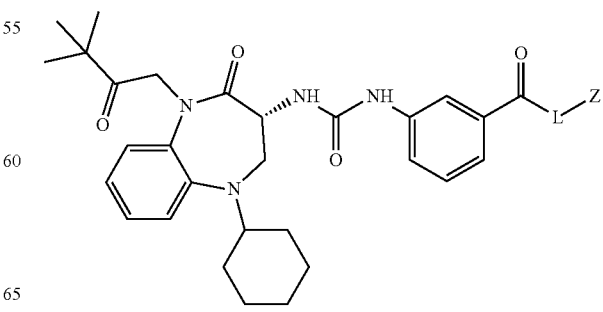

In some embodiments, B is Z-360, L is gamma (γ)-glutamate-1-tyrosine, Z is SP169.

In some embodiments compounds of the present invention have an absorption and emission maxima between about 500 nm and about 900 nm. In some embodiments compounds of the present invention have an absorption and emission maxima between about 600 nm and 800 nm.

In some embodiments compounds of the present invention are made to fluoresce after distribution thereof in the tissue cells. In some embodiments compounds of the present invention are made to fluoresce by subjecting the compounds to excitation light of near infrared wavelength. In some embodiments compounds of the present invention have a binding affinity to CCK2R or CCK2i4svR that is equal or better binding affinity of Z-360.

In certain embodiments compounds of the present invention are administered to a subject in need thereof and in some embodiments the administered composition comprises, in addition to the compound, a pharmaceutically acceptable carrier, excipient or diluent.

Some embodiments of the present invention provide methods of optical imaging of CCK2R and/or CCK2i4svR-expressing biological tissue, said method comprising:
(a) contacting the biological tissue with a composition comprising a CCK2R and/or CCK2i4svR-targeted NIR dye compound,
(b) allowing time for the compound in the composition to distribute within the biological target;
(c) illuminating the tissue with an excitation light of a wavelength absorbable by the compound; and
(d) detecting the optical signal emitted by the compound.

In some embodiments, these methods are used in detection of diseases associated with high CCK2R or CCK2i4svR, or both expression. In some embodiments, further comprising the step of constructing an image from the signal emitted in (d). In some embodiments, the invention provides the aforementioned method wherein step (a) includes two or more fluorescent compounds whose signal properties are distinguishable are contacted with the tissue, and optionally the tissue is in a subject. In some embodiments the present invention provides use of an endoscope, catheter, tomographic system, hand-held optical imaging system, surgical goggles, or intra-operative microscope for the illuminating and/or detecting method steps.

In some embodiments, compositions and methods of the present invention are used to treat cancer. In some embodiments, the cancer is selected from the group consisting of pancreatic, gastro intestinal, stomach, colon, ovarian, cervical, prostate, glioma, carcinoid, or thyroid, lung cancer, bladder cancer, liver cancer, kidney cancer, sarcoma, breast cancer, brain cancer, testicular cancer or melanoma.

In some embodiments, CCK2R and/or CCK2i4svR-targeted NIR dye compounds of the present invention are used for imaging of CCK2R and/or CCK2i4svR-expressing cells. In certain embodiments those cells are chosen from the group consisting of pancreatic, gastro intestinal, stomach, colon, ovarian, cervical, prostate, glioma, carcinoid, or thyroid, lung cancer, bladder cancer, liver cancer, kidney cancer, sarcoma, breast cancer, brain cancer, testicular cancer or melanoma cells.

The present invention also provides methods of targeting a cell type in a biological sample comprising: (a) contacting the biological sample with a CCK2R and/or CCK2i4svR-targeted NIR dye compound for a time and under conditions that allow for binding of the compound to at least one cell of the target cell type; and (b) optically detecting the presence or absence of the compound of in the biological sample, wherein presence of the compound in detecting step (b) indicates that the target cell type is present in the biological sample. In some embodiments the present invention provides methods for optical detection of CCK2R and/or CCK2i4svR-expressing cells comprising administering CCK2R and/or CCK2i4svR-targeting NIR dye compounds of the present invention and subjecting the compound to an excitation light source and detecting fluorescence from the compound. In some embodiments, the excitation light source is near-infrared wavelength light. In some embodiments the excitation light wavelength is within a range from about 600 to 1000 nanometers. In some embodiments the excitation light wavelength is within a range from about 670 to 850 nanometers.

In certain embodiments the present invention provides methods of performing image guided surgery on a subject comprising:
a) administering a composition comprising a CCK2R and/or CCK2i4svR-targeting NIR dye compound under conditions and for a time sufficient for the compound to accumulate at a given surgical site;
b) illuminating the compound to visualize the compound using infrared light; and
c) performing surgical resection of the areas that fluoresce upon excitation by the infrared light.

In some embodiments methods of the present invention the infrared light wavelength is within a range from about 600 to 1000 nanometers. In some embodiments methods of the present invention use an infrared light wavelength is within a range from about 670 to 850 nanometers.

Some embodiments of the present invention provide a method of diagnosing a disease in a subject comprising:
a) administering to a subject in need of diagnosis an amount of a CCK2R and/or CCK2i4svR-targeted NIR dye compound for a time and under conditions that allow for binding of the compound to at least one CCK2R or CCK2i4svR, or both—expressing cell;
b) measuring the signal from the compound of present in the biological sample;
c) comparing the signal measured in b) with at least one control data set, wherein the at least one control data set comprises signals from the compound of claim 1 contacted with a biological sample that does not comprise the target cell type; and
d) providing a diagnosis of disease wherein the comparison in step c) indicates the presence of the disease.

Some embodiments of the present invention provide a kit comprising a CCK2R and/or CCK2i4svR-targeting NIR dye compound. In some embodiments, the kit is used for the imaging of CCK2R-expressing cells. In some embodiments the CCK2R and/or CCK2i4svR-expressing cells are tumor cells. In some embodiments the CCK2R and/or CCK2i4svR-expressing cells are non-prostate cancer cells. In certain embodiments the CCK2R and/or CCK2i4svR-expressing cells are pancreatic or gastrointestinal, or thyroid tumor cells. In certain embodiments the CCK2R and/or CCK2i4svR-expressing cells are cancer cells. In some embodiments the present invention is used for detection of metastatic disease. In some embodiments compounds of the present invention are used for improved surgical resection and/or improved prognosis. In some embodiments methods of the present invention provide cleaner surgical margins than non-NIR compounded fluorescing dyes. In some embodiments CCK2R and/or CCK2i4svR-targeted NIR dye compounds of the present invention have an improved tumor-to-background ratio.

In a further embodiment of the methods provided, the CCK2R and/or CCK2i4svR-expressing cancer cells are of a tumor. In still a further embodiment of the methods provided, the CCK2R and/or CCK2i4svR-expressing cancer is a tumor.

In some embodiments the present disclosure relates to CCK2R and/or CCK2i4svR-targeted compounds to near-infra red (NIR) dyes and methods for their therapeutic and diagnostic use. More specifically, this disclosure provides compounds and methods for diagnosing and treating diseases associated with cells expressing CCK2R or CCK2i4svR, or both, such as pancreatic, gastro intestinal, stomach, colon, ovarian, cervical, prostate, glioma, carcinoid, or thyroid, lung cancer, bladder cancer, liver cancer, kidney cancer, sarcoma, breast cancer, brain cancer, testicular cancer or melanoma, and related diseases. The disclosure further describes methods and compositions for making and using the compounds, methods incorporating the compounds, and kits incorporating the compounds. It has been discovered that a CCK2R and/or CCK2i4svR-targeted compound, such as PS230 (a,b), PS231, PS232, and Z-360 compounded to an NIR dye via a linker (L) may be useful in the imaging, diagnosis, and/or treatment of pancreatic, gastrointestinal, thyroid cancers, and related diseases that involve pathogenic cell populations expressing or over-expressing CCK2R or CCK2i4svR, or both. Accordingly, it has been discovered that certain compounds that include a linker having a predetermined length, and/or a predetermined diameter, and/or preselected functional groups along its length may be used to treat, image, and/or diagnose such diseases.

In one illustrative embodiment, the linker L may be a releasable or non-releasable linker. In one aspect, the linker L is at least one amino acid or 4 atoms in length. In one variation, the linker L is at least about 10 atoms in length.

In an alternative aspect, the linker L is at least about 5 angstroms (Å) in length.

In another embodiment, pharmaceutical compositions are described herein, where the pharmaceutical composition includes the compounds described herein in amounts effective to treat diseases and disease states, diagnose diseases or disease states, and/or image tissues and/or cells that are associated with pathogenic populations of cells expressing or over expressing CCK2R or CCK2i4svR, or both. Illustratively, the pharmaceutical compositions also include one or more carriers, diluents, and/or excipients.

In another embodiment, methods for treating diseases and disease states, diagnosing diseases or disease states, and/or imaging tissues and/or cells that are associated with pathogenic populations of cells expressing or over expressing CCK2R or CCK2i4svR, or both are described herein. Such methods include the step of administering the compounds described herein, and/or pharmaceutical compositions containing the compounds described herein, in amounts effective to treat diseases and disease states, diagnose diseases or disease states, and/or image tissues and/or cells that are associated with pathogenic populations of cells expressing or over expressing CCK2R or CCK2i4svR, or both.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

I. Definitions

Figure 1:
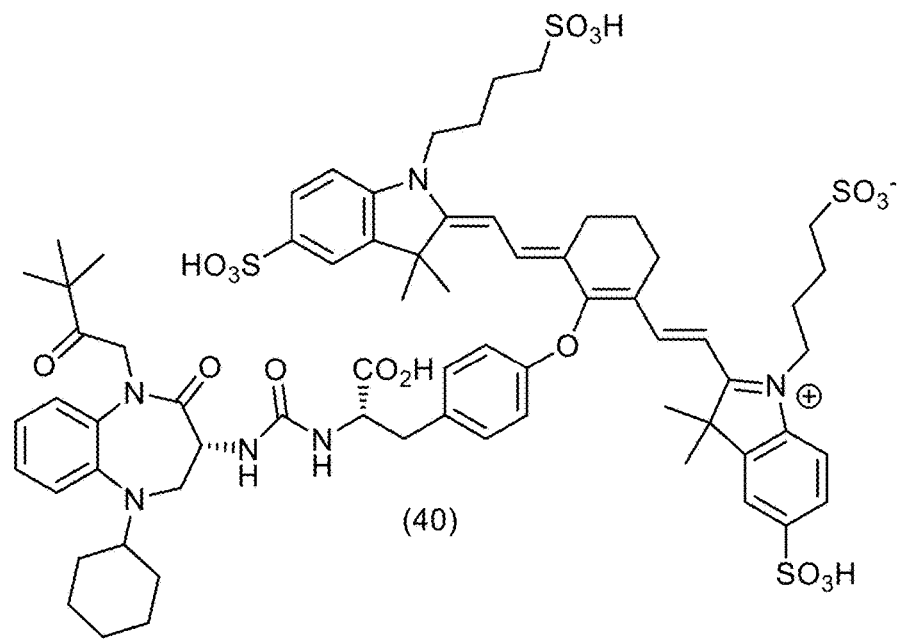
FIG. 1 depicts the chemical structures of CCK2R-targeted NIR compounds 40 and 41.
Figure 1:
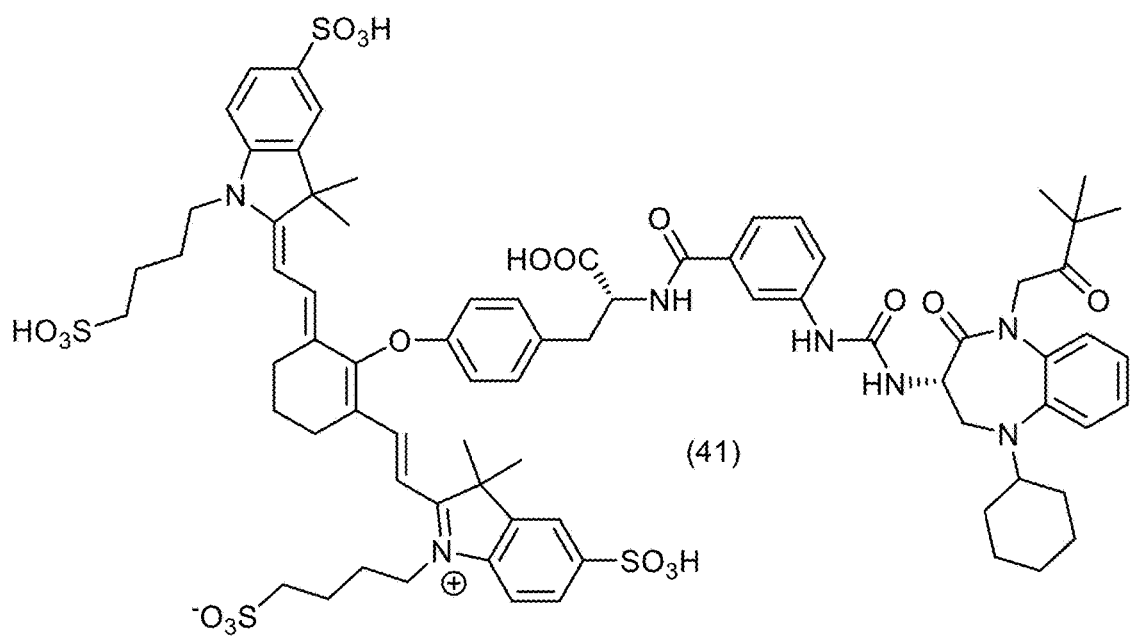
Figure 2A:
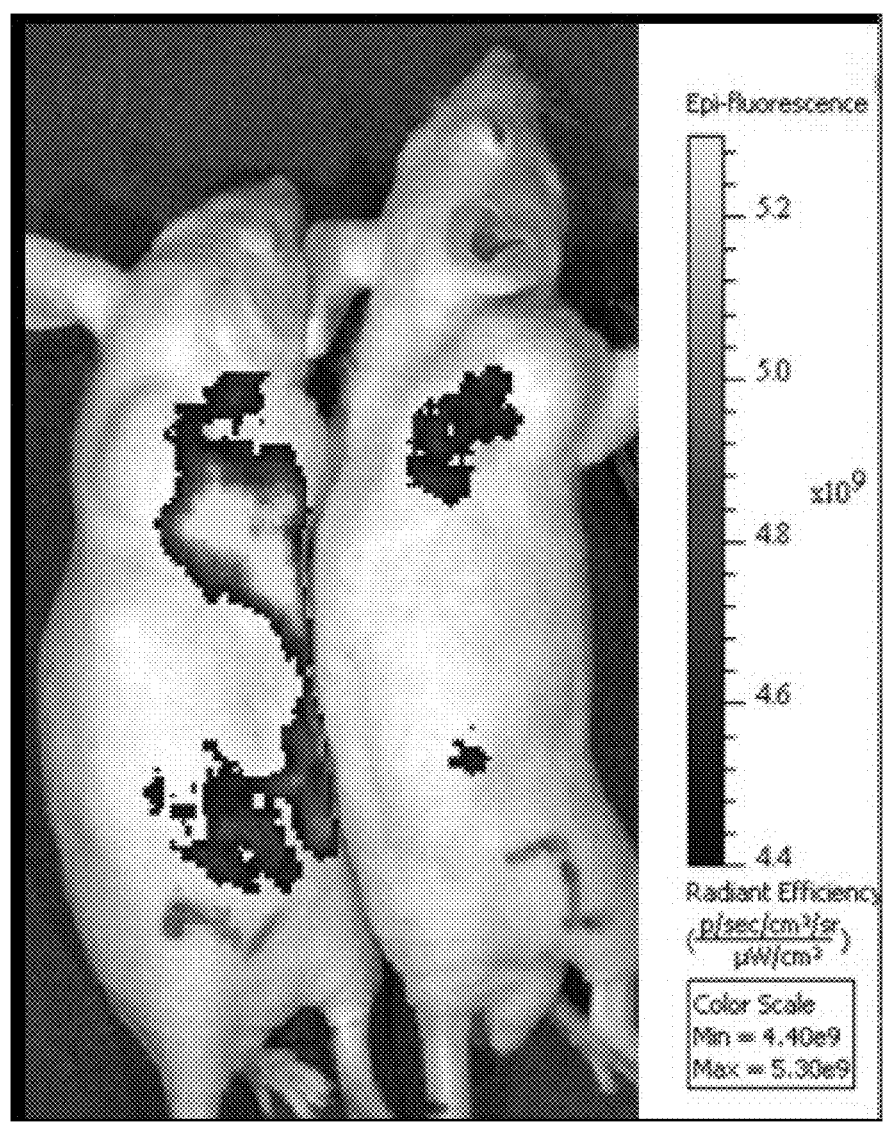
FIG. 2A illustrates the overlay of whole body fluorescence image over white light images after adjusting the threshold for compound 40. HEK-CCK2R tumor xenograft bearing mice were injected with 10 nmol of compound 1 and imaged with IVIS imager (ex=745 nm, em=ICG, exposure time=1 s) at 2 h post-injection. After imaging, selected tissues were harvested, and tissues were imaged with IVIS imager (ex=745 nm, em=ICG, exposure time=1 s).
Figure 2B:
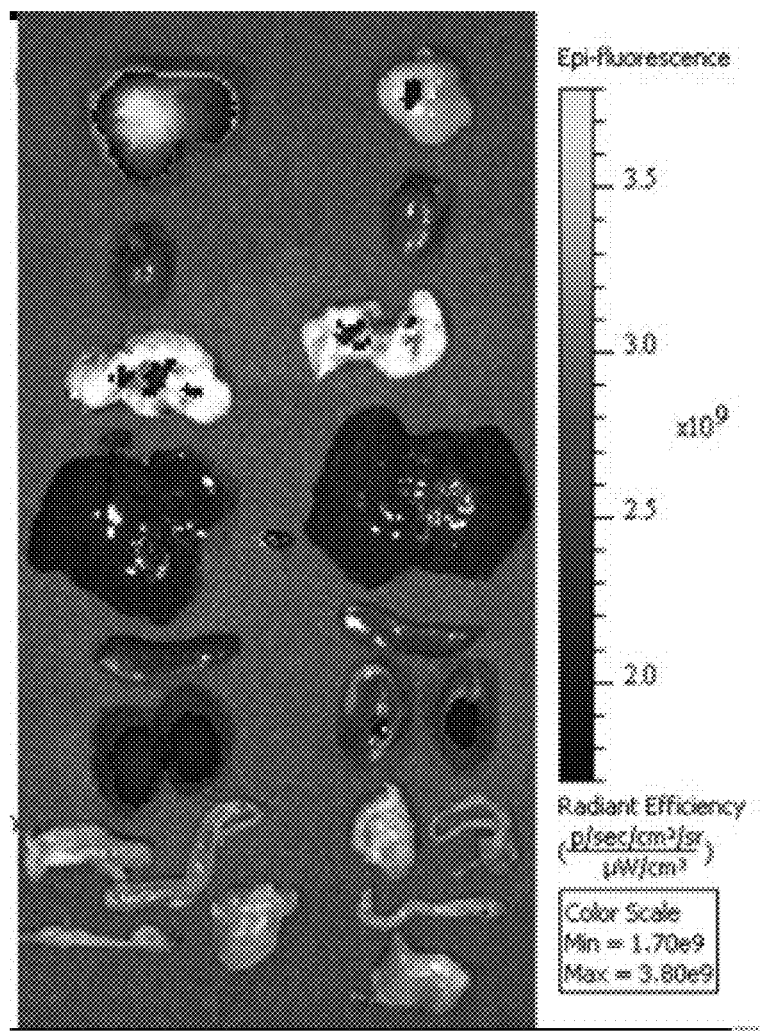
FIG. 2B shows the ex vivo tissue biodistribution analysis of FIG. 2A.
Figure 2C:
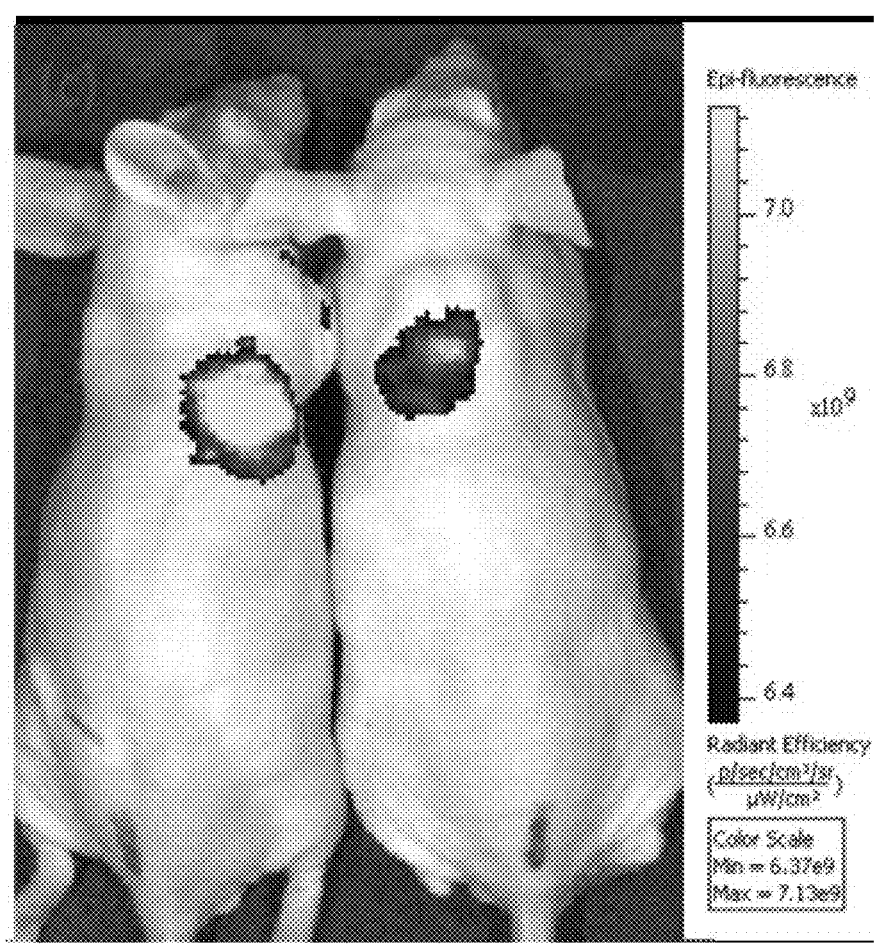
FIG. 2C depicts the overlay of whole body fluorescence image over white light images after adjusting the threshold for compound 41. HEK-CCK2R tumor xenograft bearing mice were injected with 10 nmol of compound 2 and imaged with IVIS imager (ex=745 nm, em=ICG, exposure time=1 s) at 2 h post-injection. After imaging, selected tissues were harvested, and tissues were imaged with IVIS imager (ex=745 nm, em=ICG, exposure time=1 s).
Figure 2D:
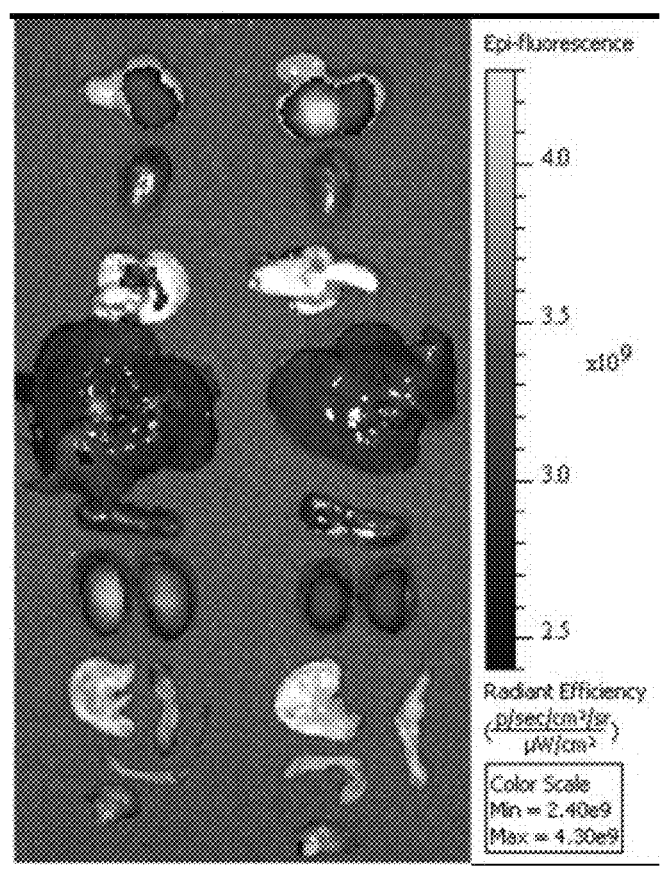
FIG. 2D illustrates the ex vivo tissue biodistribution analysis of FIG. 2C.
Figure 3A:
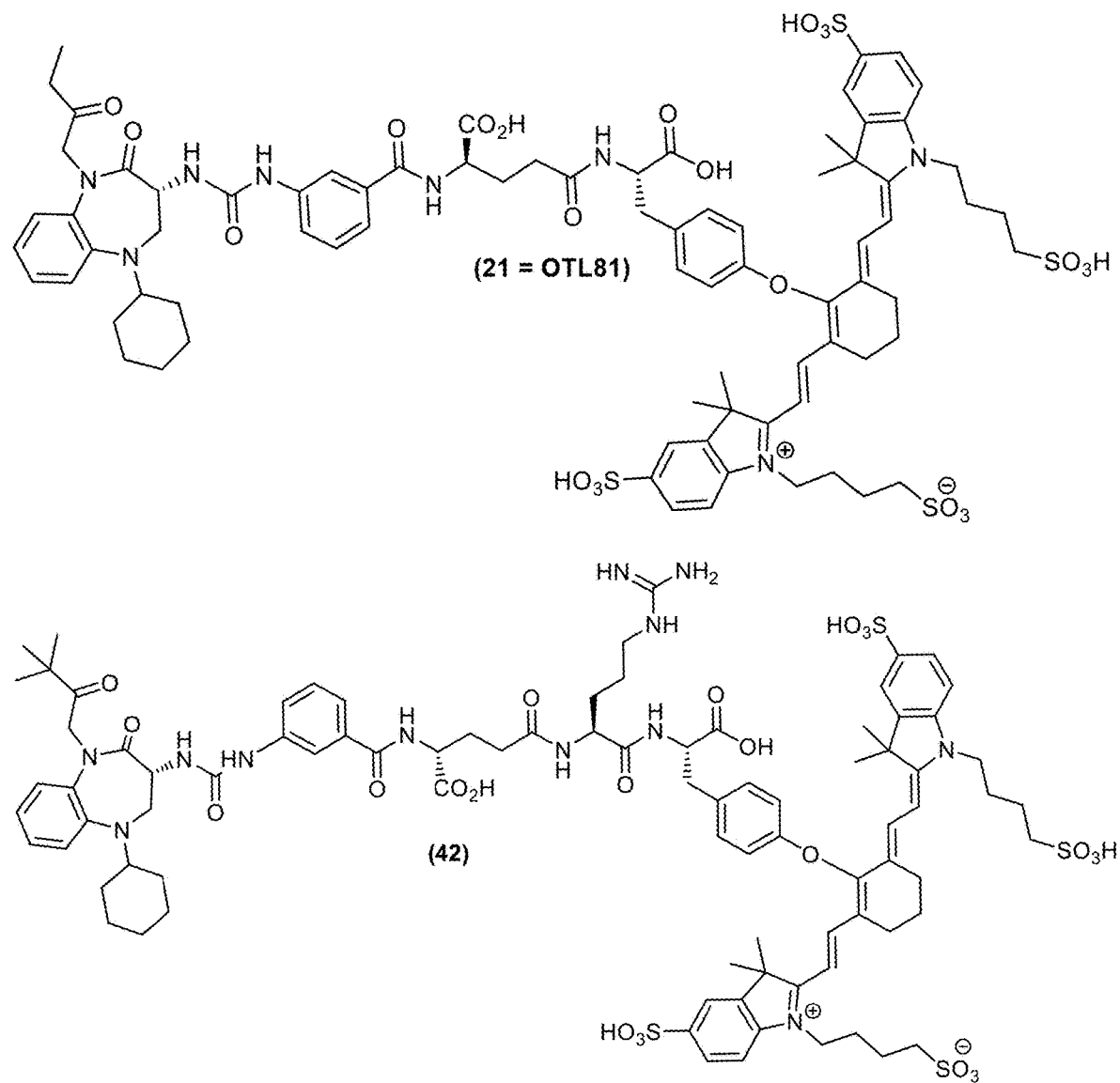
FIG. 3 shows the chemical structures of CCK2R-targeted NIR compounds 21, 42-44.
Figure 3B:
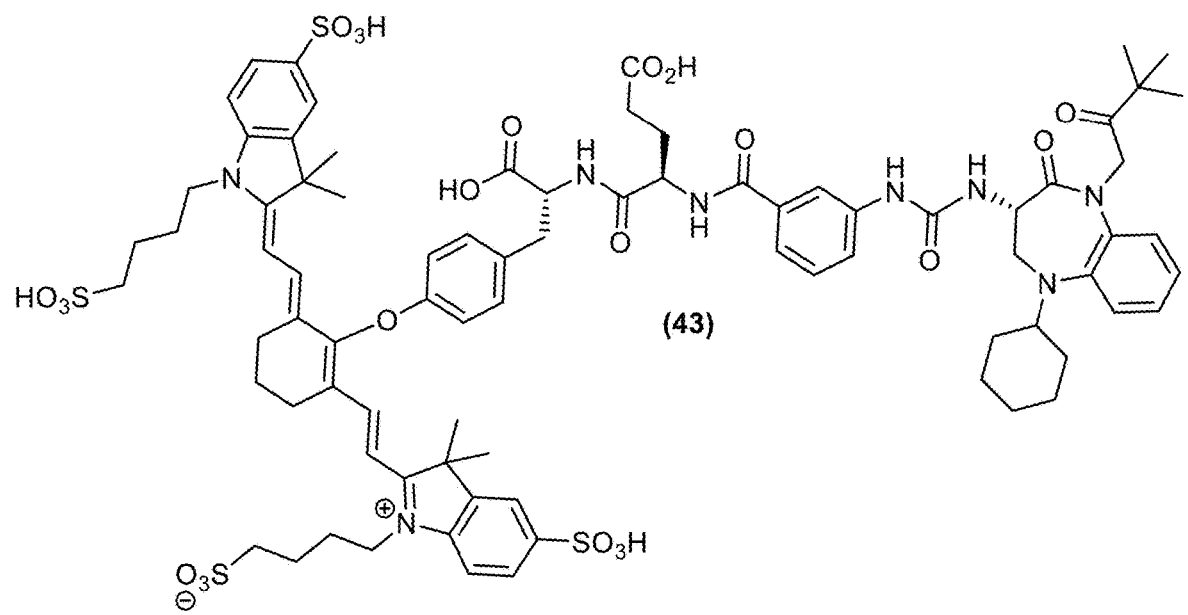
Figure 3B:
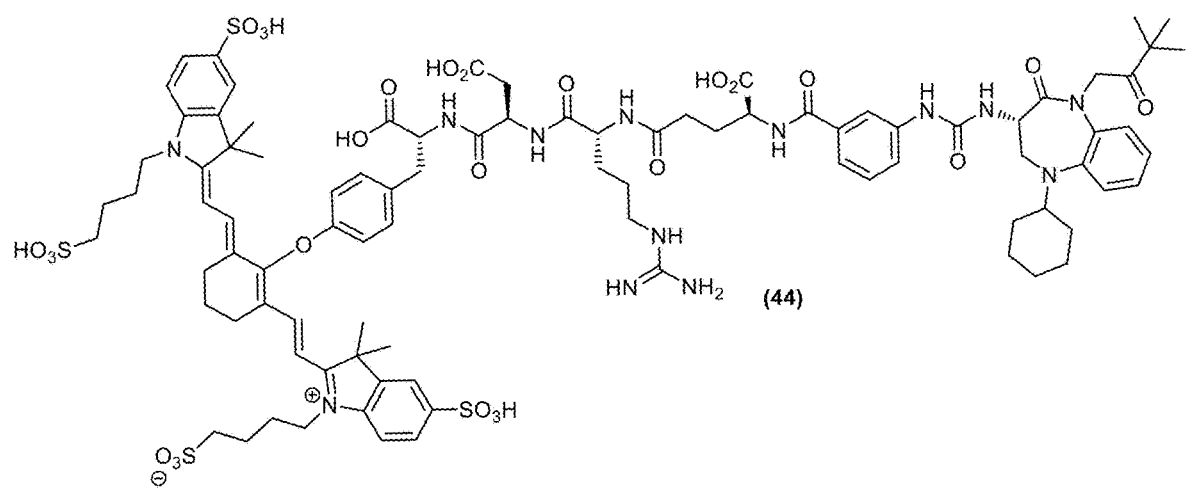
Figure 4:
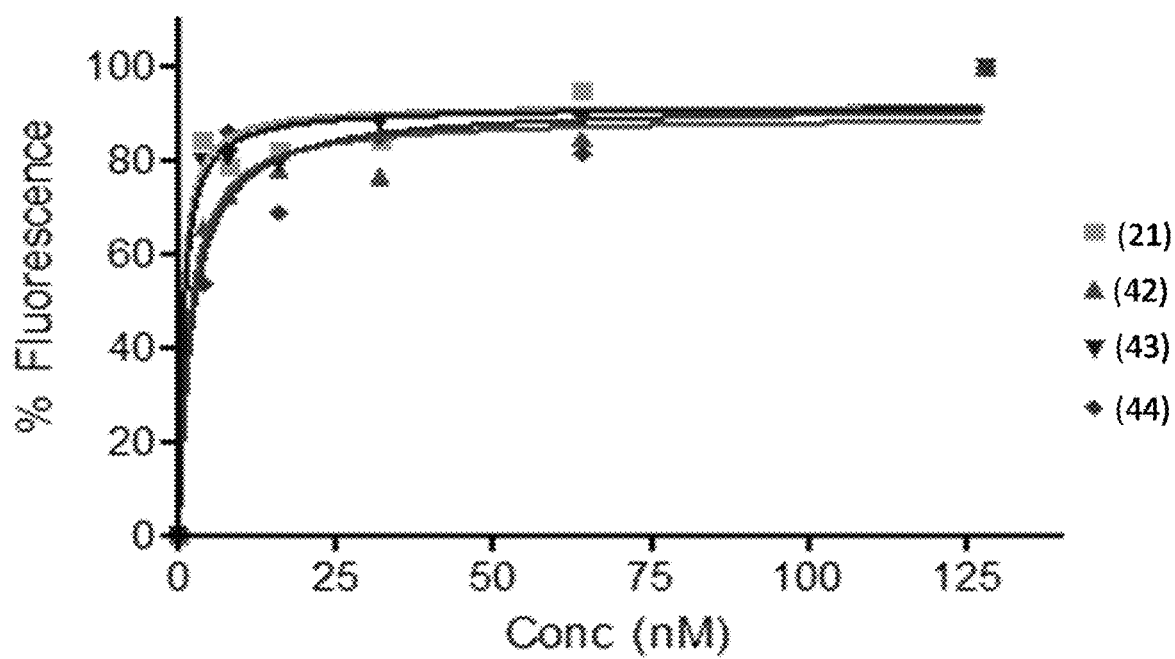
FIG. 4 depicts the binding affinities of CCK2R-NIR compounds 21, 42-44 to CCK2R. CCK2R-positive HEK-CCK2R cancer cells were incubated for 1 h at 37° C. with increasing concentrations of compounds. Media was then removed, washed with fresh media three times, and replaced with PBS. Cell bound fluorescence was assayed as using fluorometer.
Figure 5A:
FIG. 5A illustrates the analysis of compound 21 overlay of whole body fluorescence image over white light images after adjusting the threshold. HEK-CCK2R tumor xenograft bearing mice were injected with 10 nmol of 21 and imaged with IVIS imager (ex=745 nm, em=ICG, exposure time=1 s) at 2 h post-injection. After imaging, selected tissues were harvested, and tissues were imaged with IVIS imager (ex=745 nm, em=ICG, exposure time=1 s).
Figure 5B:
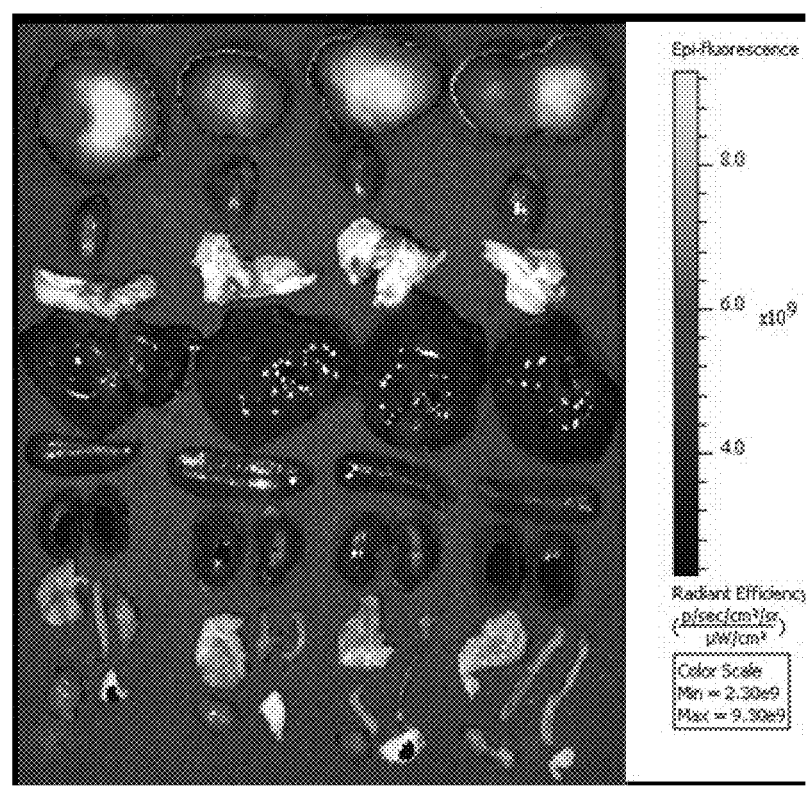
FIG. 5B shows the ex vivo tissue biodistribution analysis of FIG. 5A.
Figure 6A:
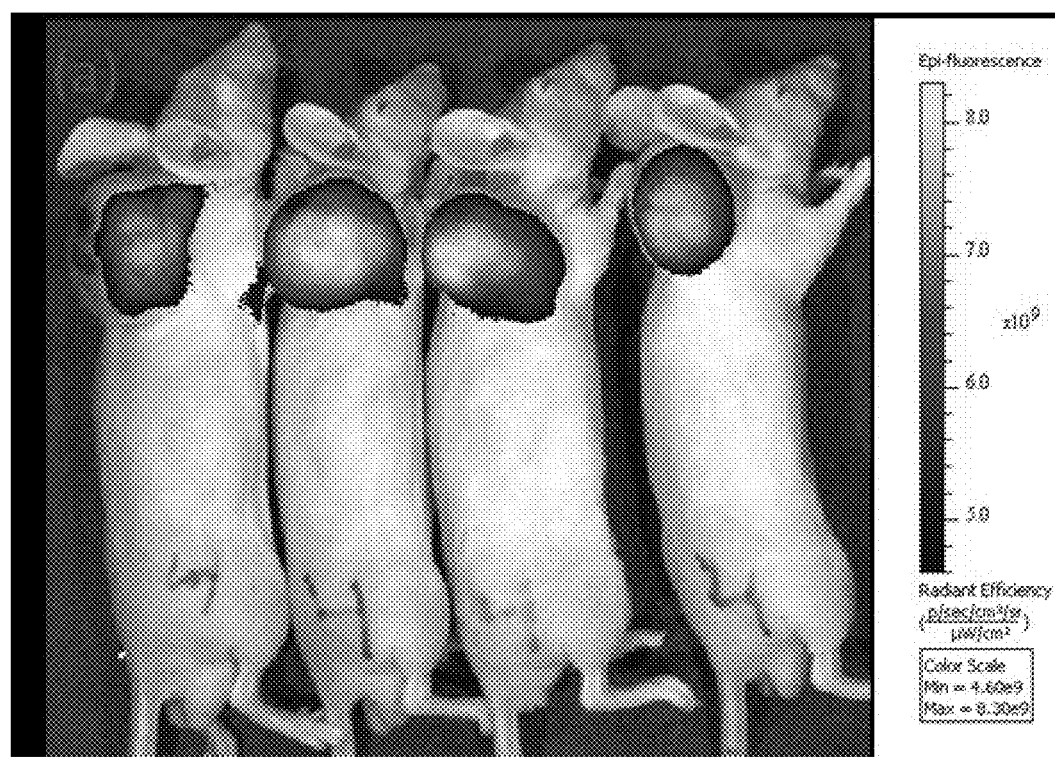
FIG. 6A depicts the analysis of compound 42: overlay of whole body fluorescence image over white light images after adjusting the threshold. HEK-CCK2R tumor xenograft bearing mice were injected with 10 nmol of 42 and imaged with IVIS imager (ex=745 nm, em=ICG, exposure time=1 s) at 2 h post-injection. After imaging, selected tissues were harvested, and tissues were imaged with IVIS imager (ex=745 nm, em=ICG, exposure time=1 s).
Figure 6B:
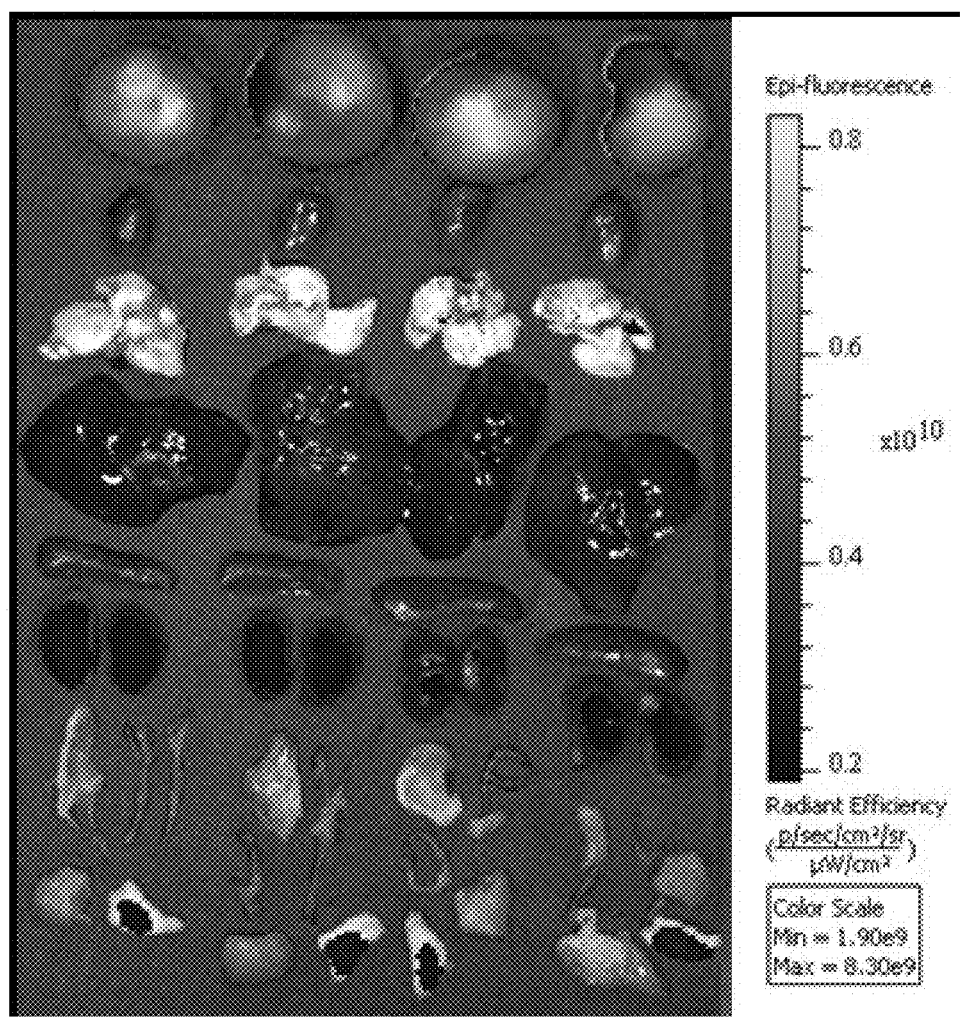
FIG. 6B illustrates the ex vivo tissue biodistribution analysis of FIG. 6A.
Figure 7A:
FIG. 7A shows the analysis of compound 43: overlay of whole body fluorescence image over white light images after adjusting the threshold. HEK-CCK2R tumor xenograft bearing mice were injected with 10 nmol of 43 and imaged with IVIS imager (ex=745 nm, em=ICG, exposure time=1 s) at 2 h post-injection. After imaging, selected tissues were harvested, and tissues were imaged with IVIS imager (ex=745 nm, em=ICG, exposure time=1 s).
Figure 7B:
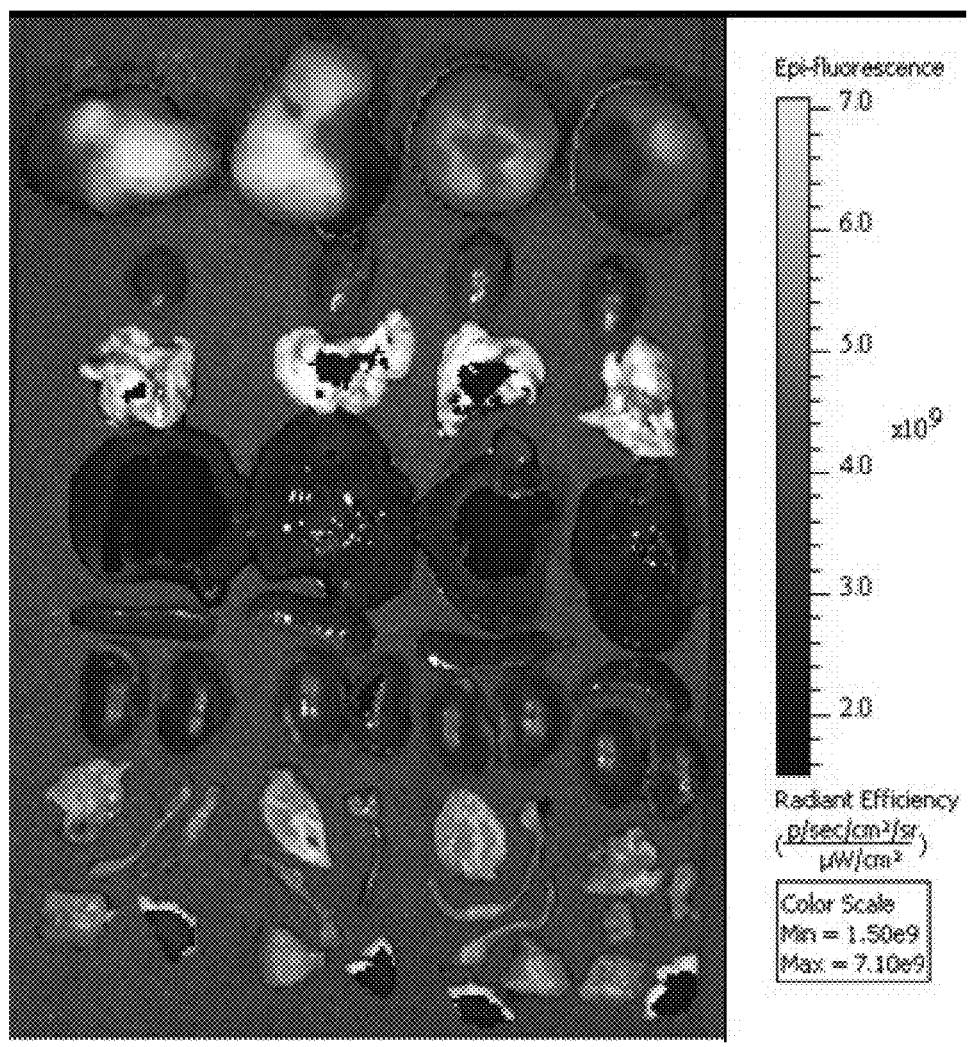
FIG. 7B depicts the ex vivo tissue biodistribution analysis of FIG. 7A.
Figure 8A:
FIG. 8A illustrates the analysis of compound 44: overlay of whole body fluorescence image over white light images after adjusting the threshold. HEK-CCK2R tumor xenograft bearing mice were injected with 10 nmol of 44 and imaged with IVIS imager (ex=745 nm, em=ICG, exposure time=1 s) at 2 h post-injection. After imaging, selected tissues were harvested, and tissues were imaged with IVIS imager (ex=745 nm, em=ICG, exposure time=1 s).
Figure 8B:
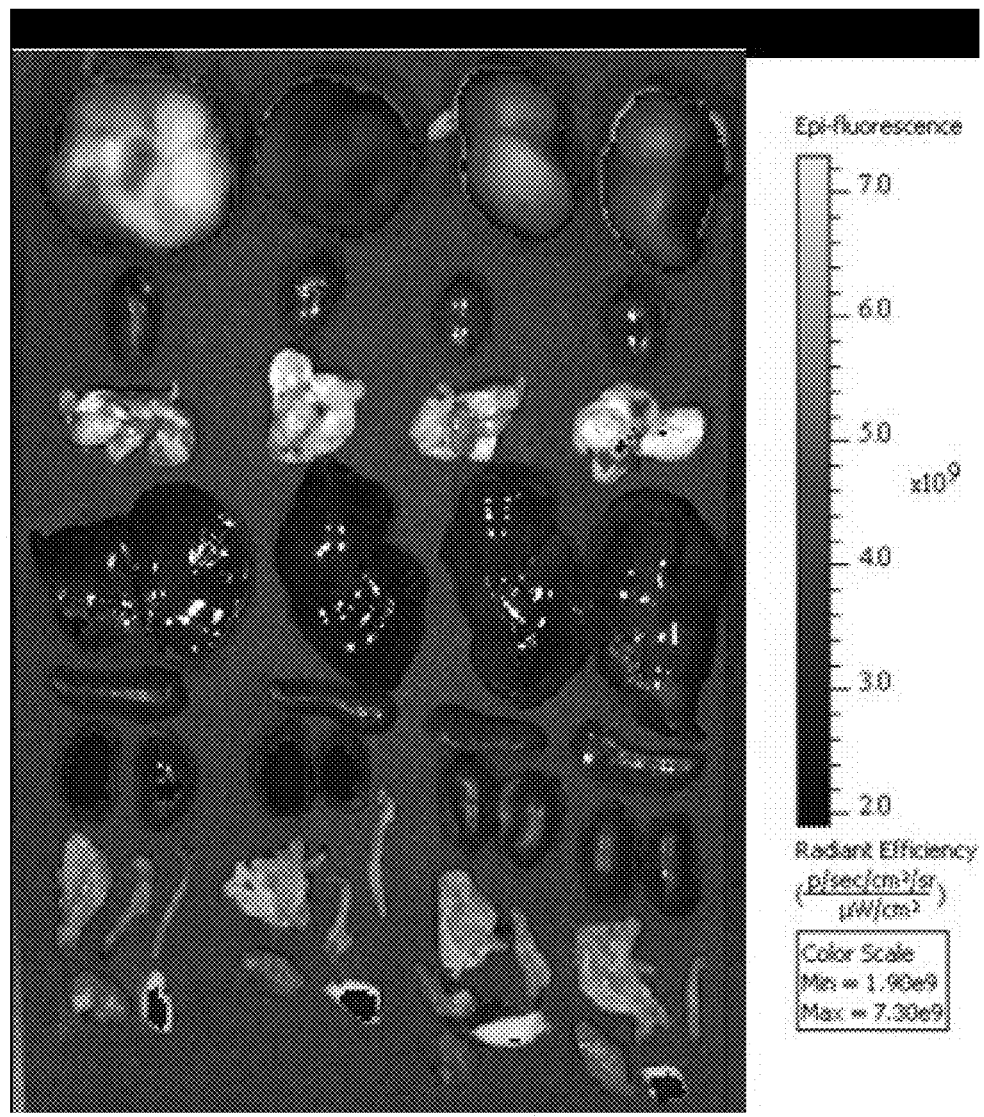
FIG. 8B shows the ex vivo tissue biodistribution analysis of compound 44.
Figure 9:
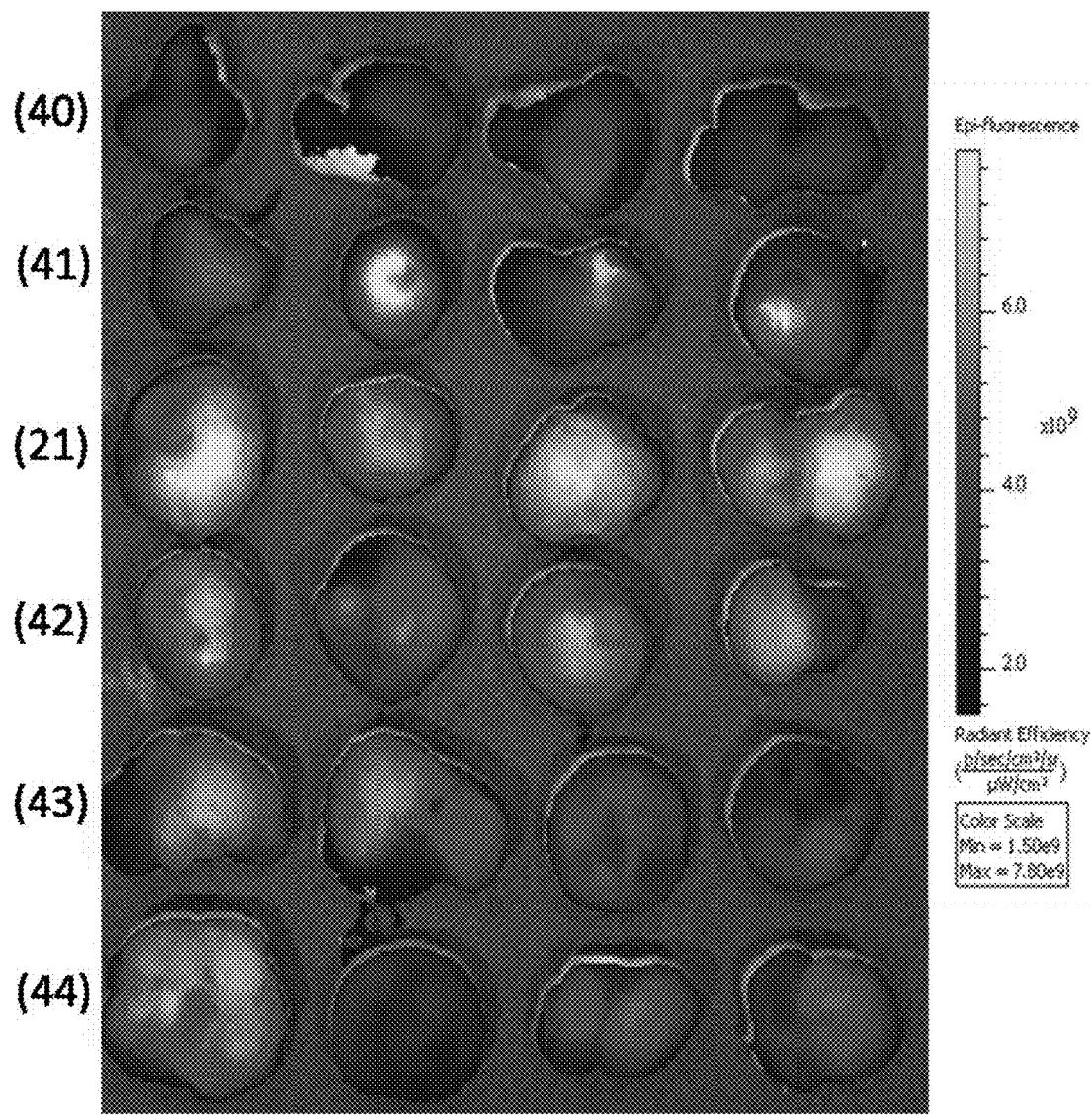
FIG. 9 depicts a head-to-head comparison of fluorescence in the tumors from the mice injected with CCK2R-targeted-NIR dye compounds 21, 40-44. Overlay of tumor fluorescence image over white light images. HEK-CCK2R tumor xenograft bearing mice were injected with 10 nmol of requisite compound and imaged with IVIS imager at 2 h post-injection. After imaging, tumor tissues were harvested, and imaged with IVIS imager (ex=745 nm, em=ICG, exposure time=1 s).
Figure 10A:
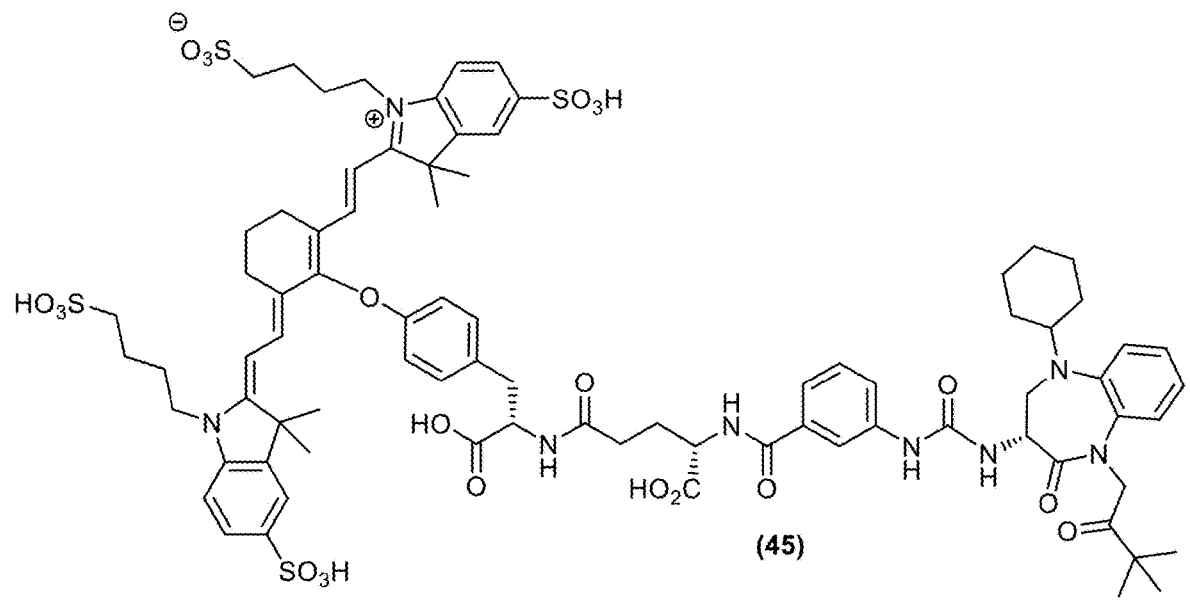
FIG. 10 illustrates the chemical structures of CCK2R-targeted NIR compounds 45-49.
Figure 10A:
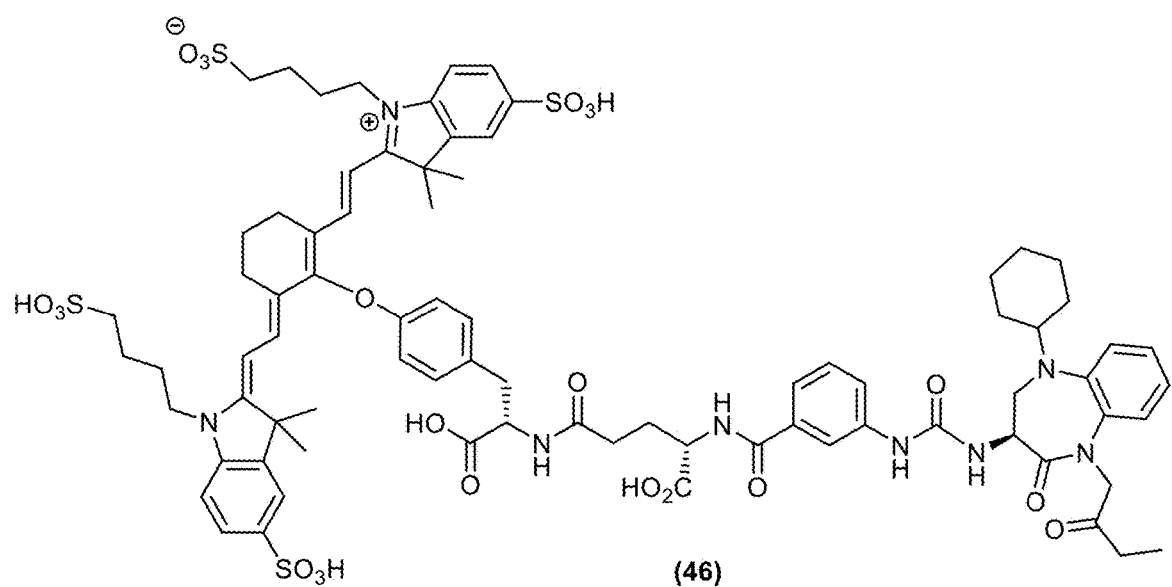
Figure 10B:
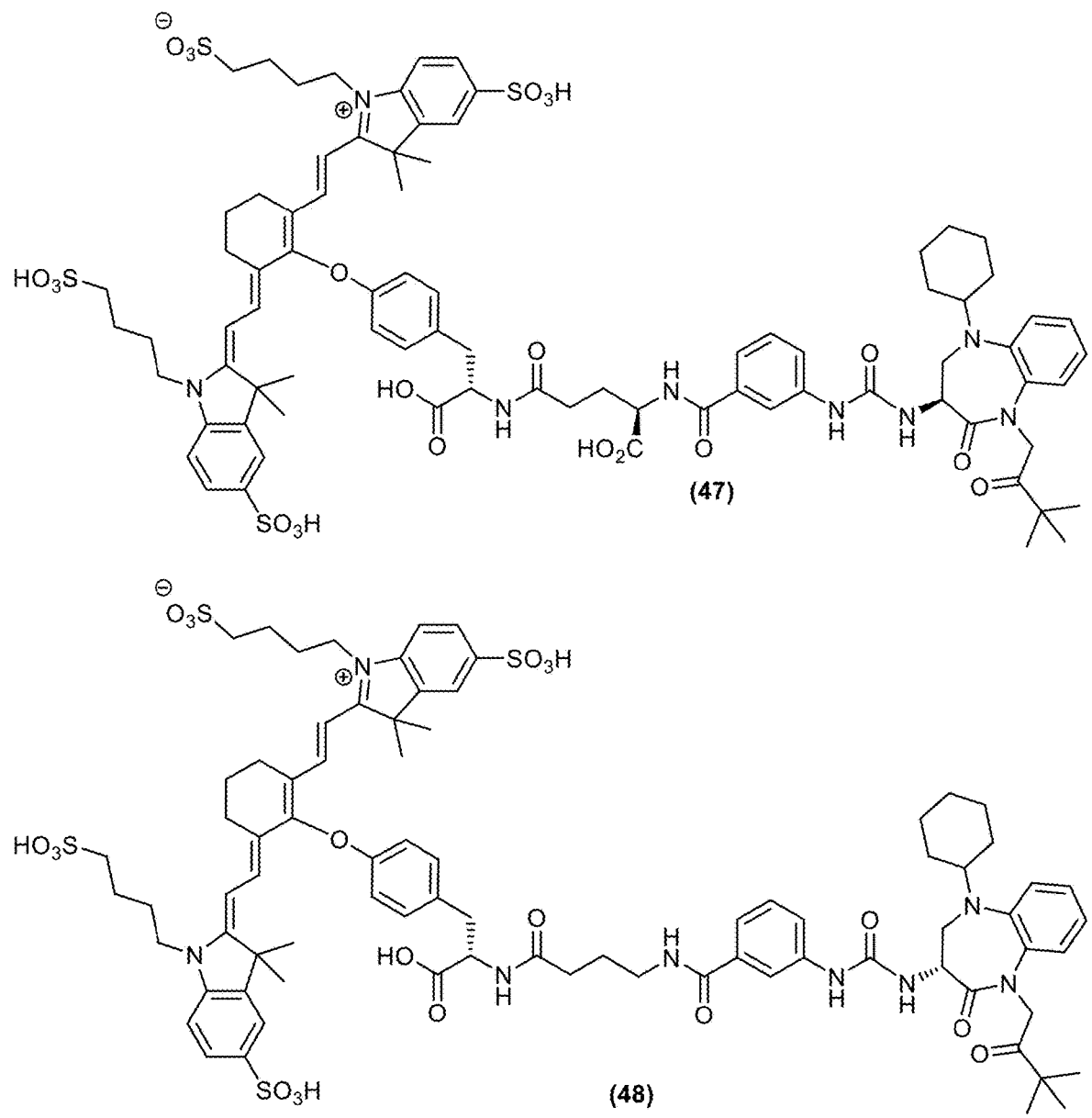
Figure 10C:
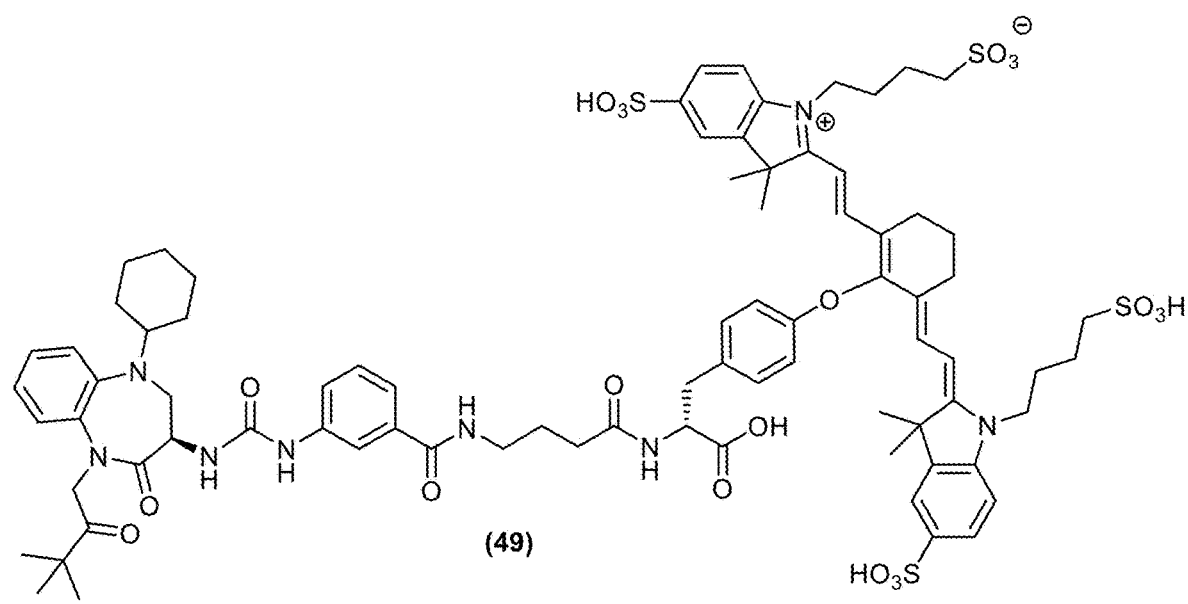
Figure 11:
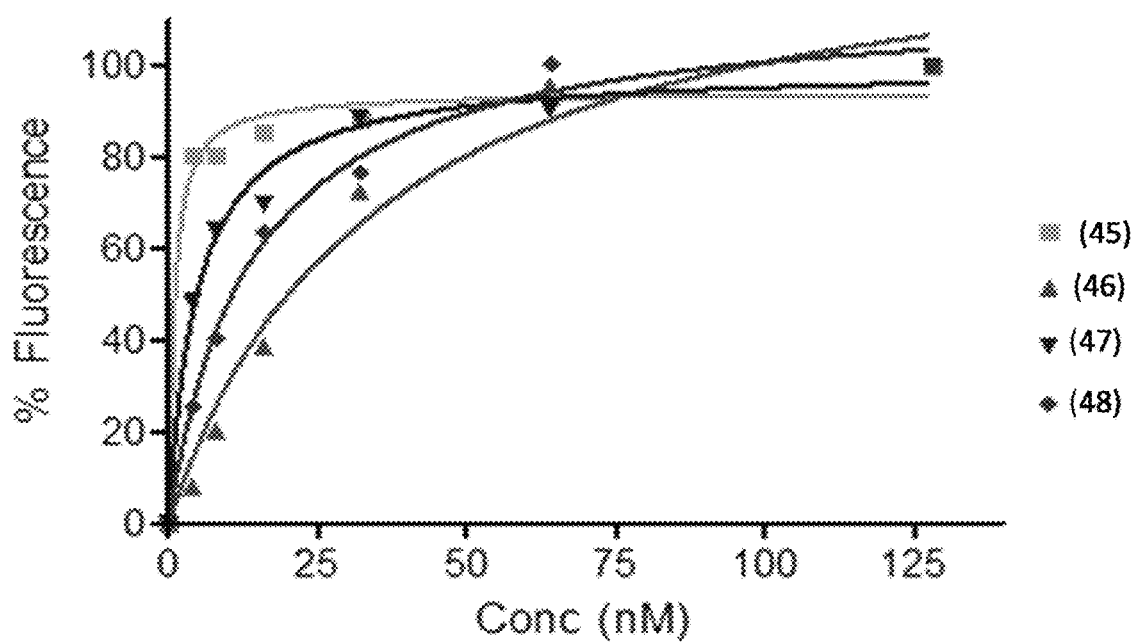
FIG. 11 shows the binding affinities of CCK2R-NIR compounds 45-48 to CCK2R. CCK2R-positive HEK-CCK2R cancer cells were incubated for 1 h at 37° C. with increasing concentrations of compounds. Media was then removed, washed with fresh media three times, and replaced with PBS. Cell bound fluorescence was assayed as using fluorometer.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

Unless otherwise clear by the context, each reference to CCK2R is a reference to both CCK2R and CCK2i4svR.

II. Compounds

The present invention is based on the discovery that useful imaging agents (active moieties) can be compounds via a linker to targeting ligands that selectively bind CCK2R and the splice variant CCK2i4svR. Through diligent efforts the inventors developed linkers and identified locations on the targeting ligands to which the active moieties could be linked without interfering with the ability of the targeting ligands to selectively bind CCK2R and/or CCK2i4svR. The inventors have thus developed compounds that comprise a targeting ligand linked to an active moiety, where the targeting ligand is a 2,3,4,5-tetrahydro-1H-1,4-benzodiazepine compound that selectively binds to CCK2R and/or CCK2i4svR, and the active moiety is a therapeutic agent or imaging agent.

In particular, the invention is directed to compounds comprising

B-L-Z wherein B is a targeting ligand, L is a linker, Z is an NIR imaging moiety, These compounds target and bind CCK2R or CCK2i4svR, or both.

The compounds are targeted to cells that express or over-express CCK2R or CCK2i4svR through the targeting ligand. Once delivered, the compounds bind to the receptors. In certain embodiments, the compounds remain on the surface of the cell for a period of time sufficient for detecting, imaging and/or diagnosis. In other embodiments, the compounds are internalized into the cell by endogenous cellular mechanisms, such as endocytosis, for subsequent detection, imaging and/or diagnosis, or treatment. Once internalized, the compounds may remain intact or be decomposed, degraded, or otherwise altered to allow the release of the active moiety forming the compounds. It is appreciated that in detecting, imaging and/or diagnostic configurations, the active moiety may remain attached to the compounds or be released either before or after the compounds has been internalized into the targeted cell.

In a certain aspect, the invention includes compounds that have a binding constant $K_d$ of about 5 nM or less. In another embodiment, the compounds described herein exhibit selectivity for CCK2R expressing or CCK2R over-expressing cells or tissues relative to normal tissues such as blood, lung, liver, spleen, duodenum, skin, muscle, bladder, and prostate, with at least 3-fold selectivity, or at least 5-fold selectivity. In one variation, the compounds described herein exhibit selectivity for CCK2R expressing or CCK2R over-expressing cells or tissues relative to normal tissues with at least 10-fold selectivity. It is appreciated that the selectivity observed for imaging is indicative of the selectivity that may be observed in treating disease states responsive to the selective or specific elimination of cells or cell populations that express or over-express CCK2R.

In some embodiments, the compound has the formula

B-L-Z wherein B is a ligand selected from the group consisting of

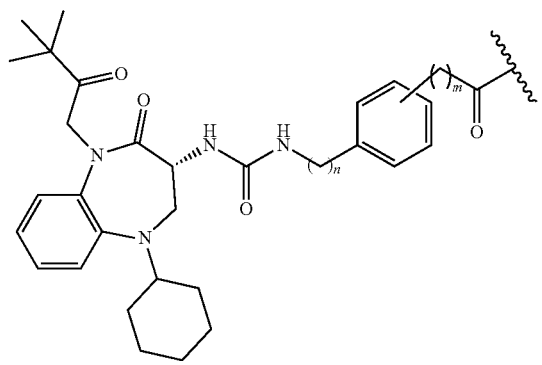

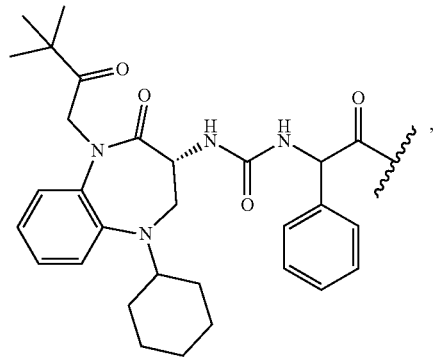

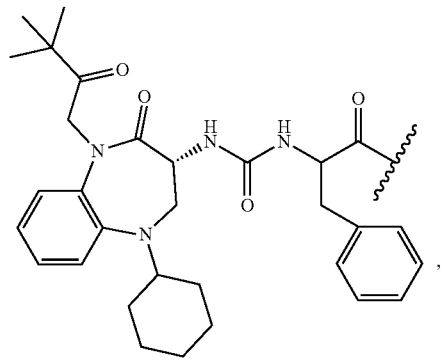

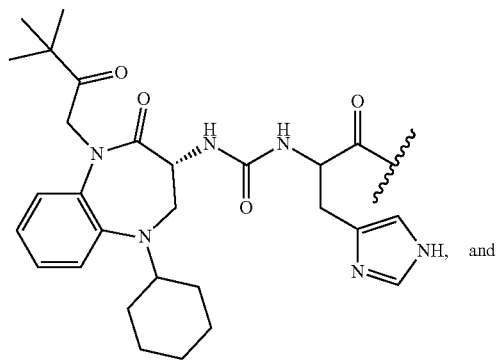

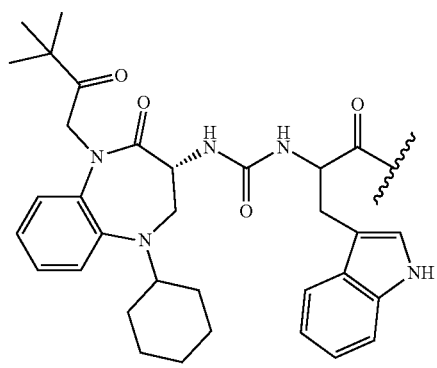 [SMILES: *C(=O)C(Cc1c[nH]c2ccccc12)NC(=O)N[C@@H]1CN(C2CCCCC2)c2ccccc2N(CC(=O)C(C)(C)C)C1=O]

wherein the values of m and n are independently selected from the values 0, 1, or 2, wherein L is a linker, and wherein Z is an imaging agent or a pharmaceutically acceptable salt thereof, or isotopes thereof.

In another embodiment L is an amino acid or an amino acid derivative. In yet a further embodiment the amino acid or amino acid derivative is selected from the group consisting of a naturally occurring amino acid or a naturally occurring amino acid derivative.

In some embodiments L is glutamic acid or gamma-aminobutyric acid.

In another embodiment L is selected from the group consisting of

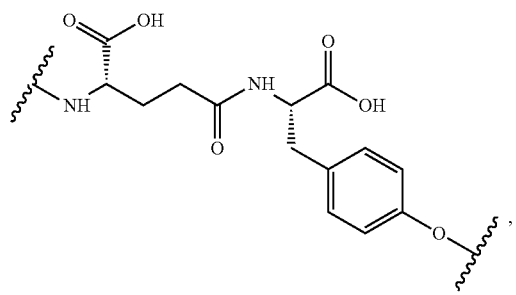

-continued

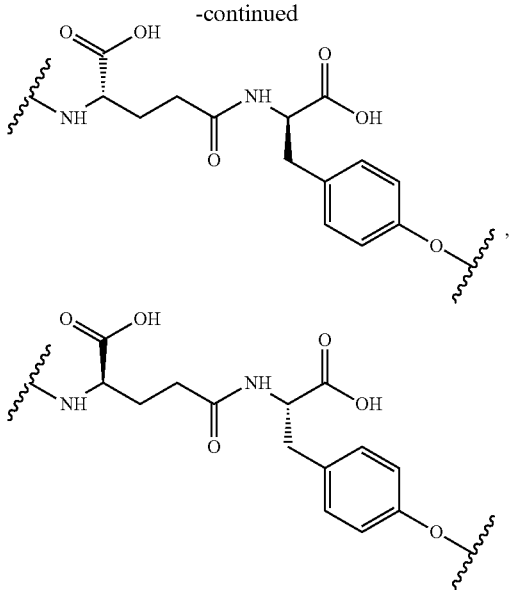

and

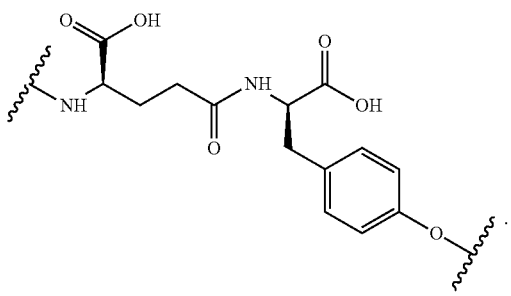

In yet another embodiment L is polyethylene glycol (PEG), PEG$_2$, or 5-amino pentanoic acid.

In some embodiments Z is represented by the formula:

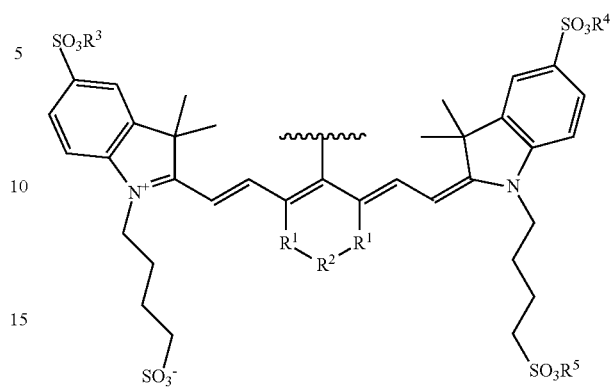

wherein, R$^1$ is independently selected from the group consisting of O, S, N and C, R$^2$ is independently selected from the group consisting of CH$_2$ and CH$_2$CH$_2$, and each of R$^3$, R$^4$, and R$^5$ are independently selected from the group consisting of H, Na, K, and NH$_4$.

In another embodiment Z has an absorption and emission maxima in the visible spectrum. In yet another embodiment Z has an absorption and emission maxima of about 680 nm to about 800 nm.

In some embodiments the compound is made to fluoresce after distribution thereof in the tissue cells. In another embodiment the compound is made to fluoresce by subjecting the compound to excitation light of near infrared wavelength. In yet another embodiment the compound is highly selective for targeting to a tumor cell.

One embodiment discloses a compound having the formula selected from the group consisting of

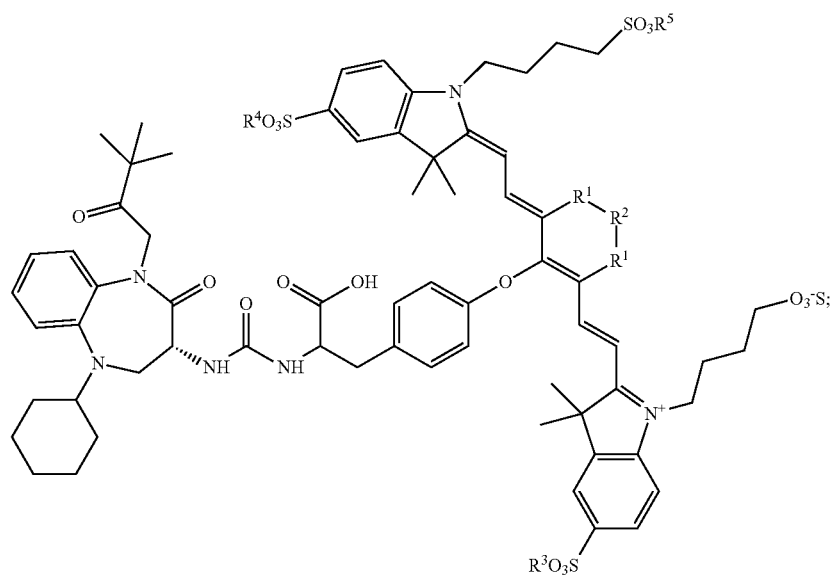

-continued
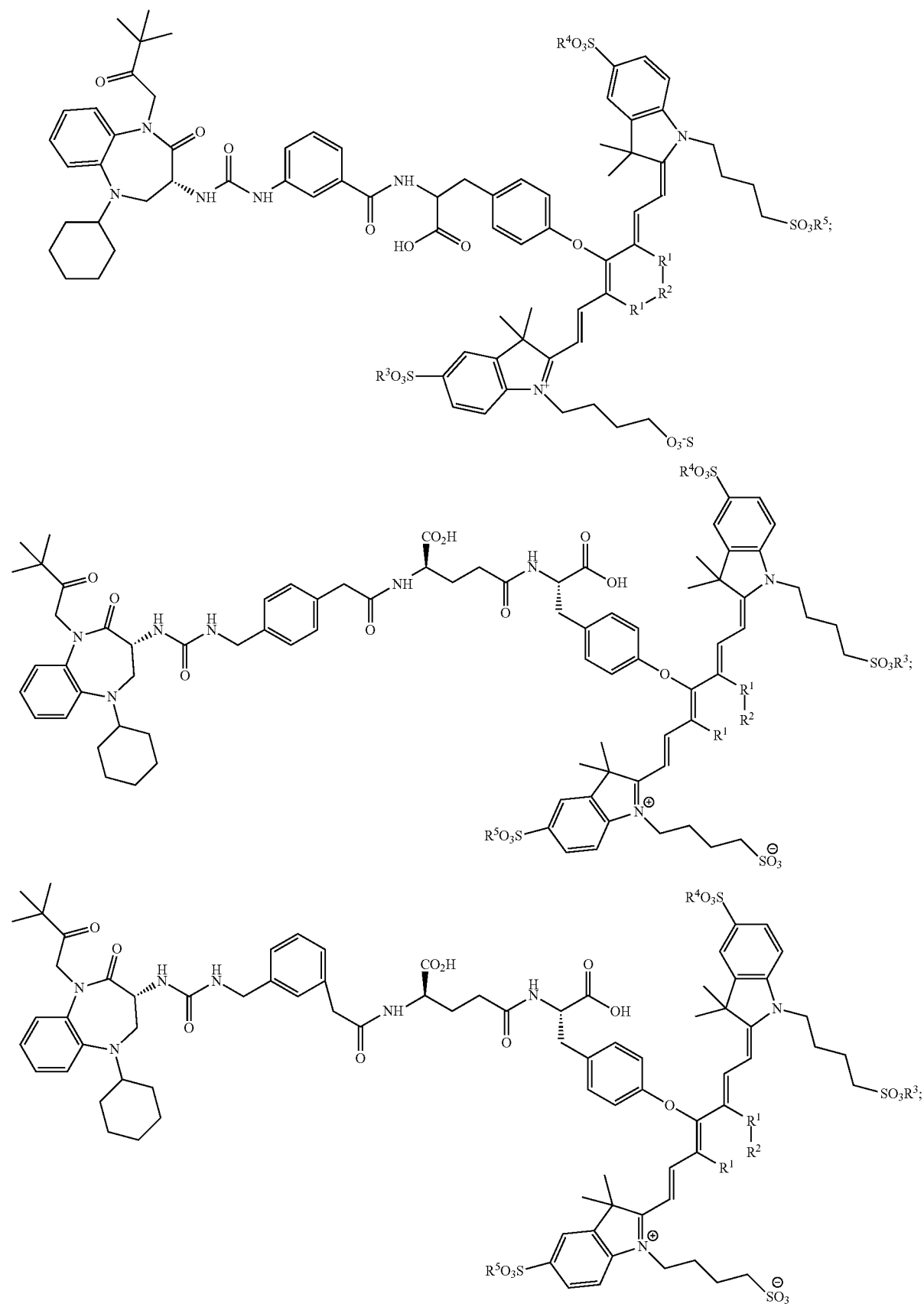

-continued
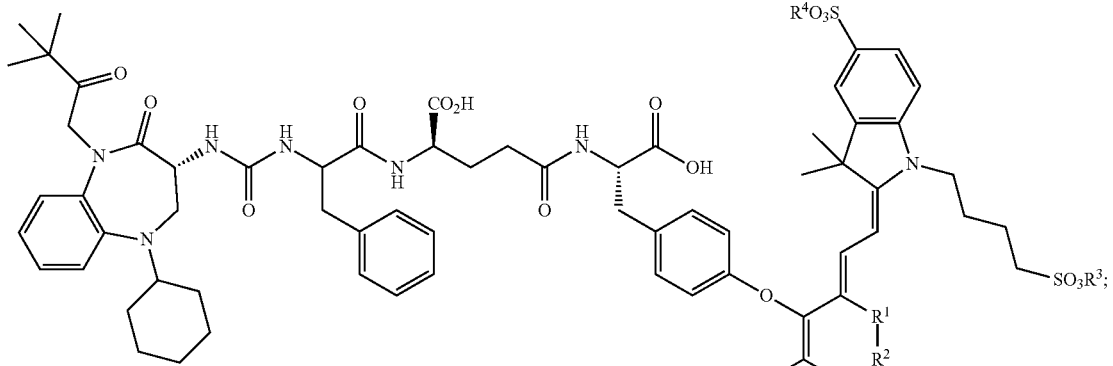
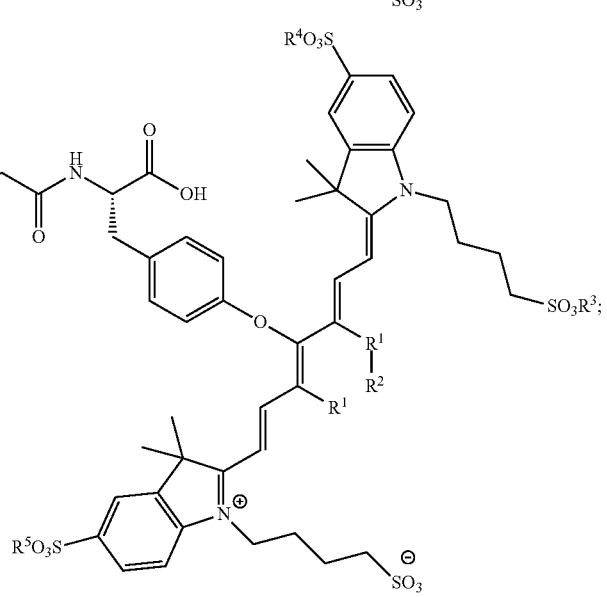
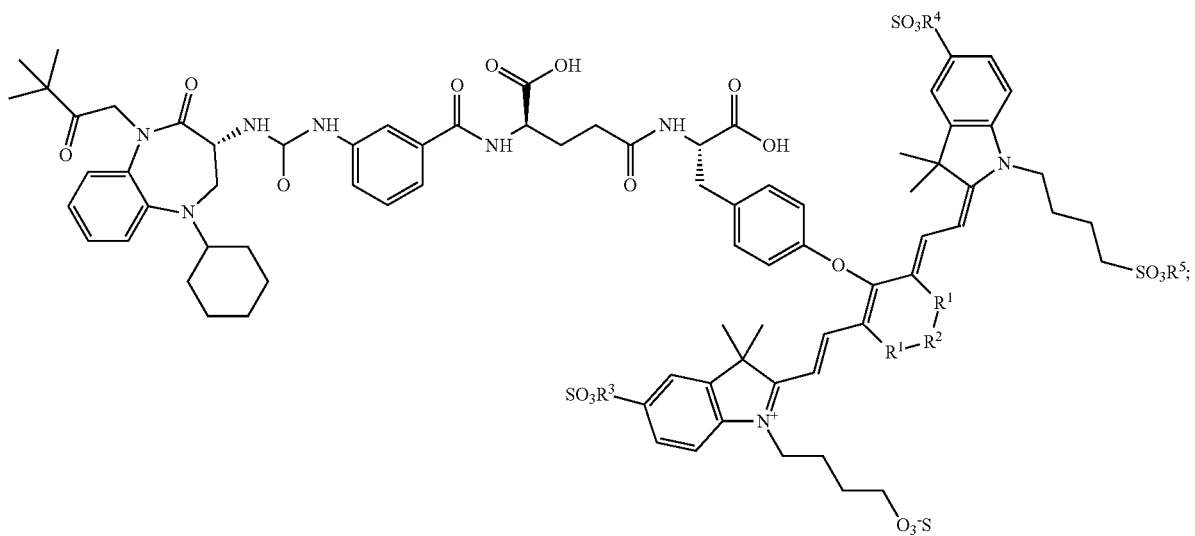

-continued
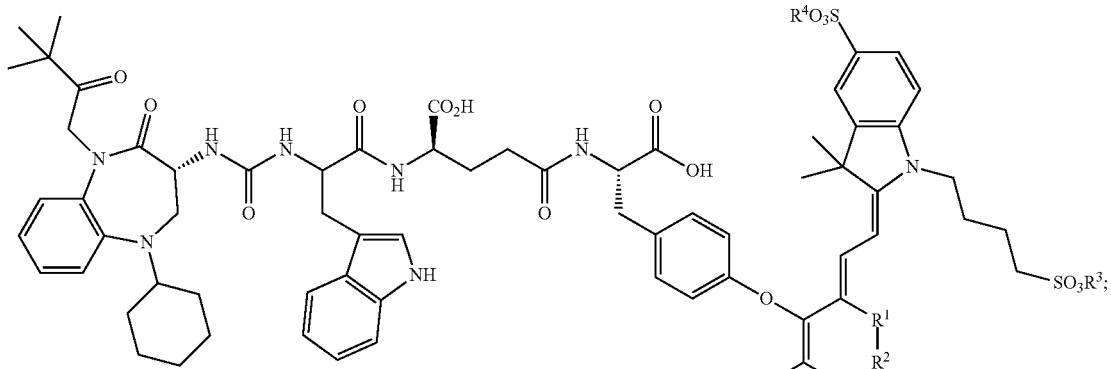
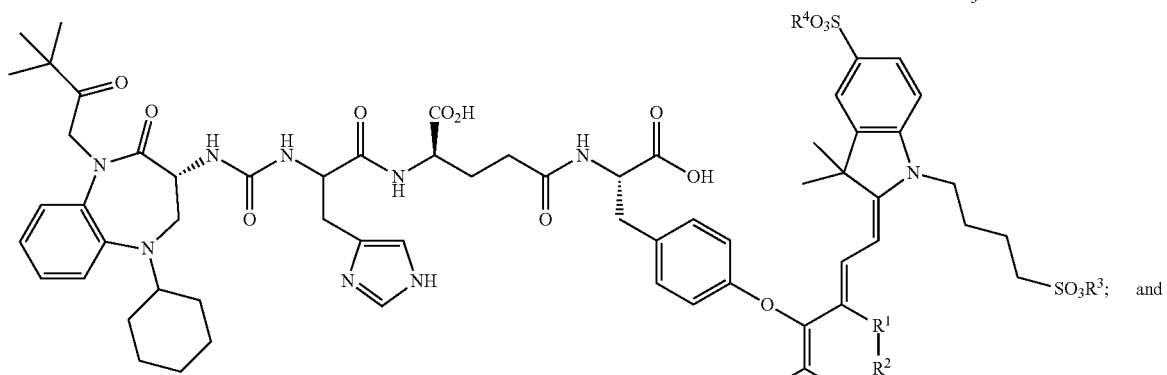
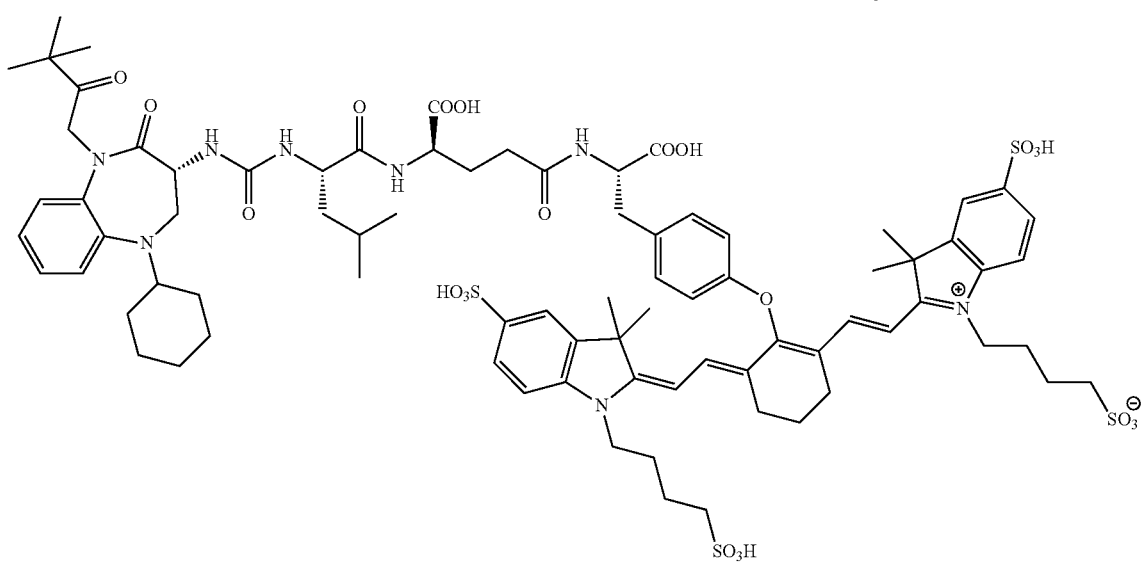

wherein, R¹ is independently selected from the group consisting of O, S, N and C,
R² is independently selected from the group consisting of $CH_2$ and $CH_2CH_2$, and
each of R³, R⁴, and R⁵ are independently selected from the group consisting of H, Na, K, and $NH_4$;
or a pharmaceutically acceptable salt thereof, or isotopes thereof.

Several embodiments disclose methods for detecting a tumor in a subject, comprising the steps of selecting a subject suspected of having a tumor, administering to said subject a compound that the formula

B-L-Z wherein B is a ligand selected from the group consisting of

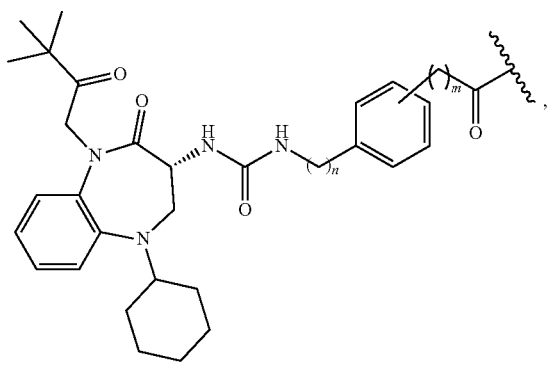

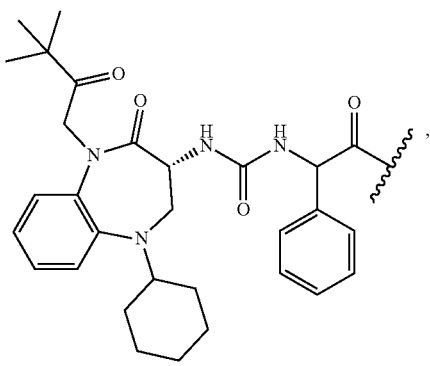

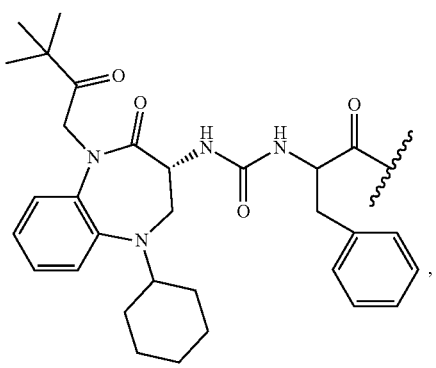

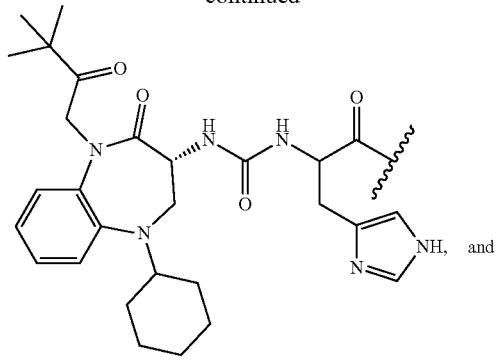

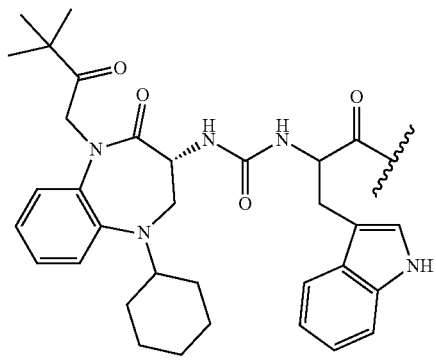 [SMILES: *C(=O)C(Cc1c[nH]c2ccccc12)NC(=O)N[C@@H]1CN(C2CCCCC2)c2ccccc2N(CC(=O)C(C)(C)C)C1=O]

wherein the values of m and n are independently selected from the values 0, 1, or 2,
wherein L is a linker, and
wherein Z is an imaging agent
or a pharmaceutically acceptable salt thereof, or isotopes thereof.

Some embodiments disclosed include a method for treating a subject having cancer comprising the steps of selecting a subject having cancer and administering at least one of the previously disclosed compounds to the subject, wherein the compound produces a therapeutic effect on the tissue or cells of the subject.

In some embodiments the subject is an animal or a human.

In a further embodiment, the method includes at least one of the previously disclosed compounds which further comprises a pharmaceutically acceptable diluent or carrier.

In some embodiments the tissue or cells are malignant and associated with a cancer selected from the group consisting of kidney cancers, medullary thyroid cancers, insulinomas, small cell lung cancers, bronchial, and ileal carcinoids, GIST tumors, and colon cancers, hepatocellular carcinomas, and pancreatic cancers. In a further embodiment the cancer is kidney cancer. In yet another embodiment the cancer is GIST cancer. And in yet another embodiment the cancer is stomach cancer.

In some embodiments the cancer is selected from the group consisting of kidney cancers, medullary thyroid cancers, insulinomas, small cell lung cancers, bronchial, and ileal carcinoids, GIST tumors, and colon cancers, hepatocellular carcinomas, and pancreatic cancers. In a further embodiment the cancer is kidney cancer. In yet another embodiment the cancer is GIST cancer. And in yet another embodiment the cancer is stomach cancer In some embodiments the tissue or cells overexpress a cholecystokinin B receptor or have diseases associated with expression or overexpression of a cholecystokinin B receptor. In yet another embodiment the cell is a CCK2 receptor expressing cell selected from the group consisting of a malignant cell, an inflammatory cell, and a microbial cell.

In some embodiments the excitation light is near-infrared wavelength light. In another embodiment the excitation light wavelength is within a range from about 600 to about 1000 nanometers. In yet another embodiment the excitation light wavelength is within a range from about 670 to about 850 nanometers.

In some embodiments at least one of the tissues or cells is resected prior to, subsequent to, or simultaneously with the administration of said composition.

In some embodiments the cancer is visualized in the subject.

Some embodiments disclosed include composition comprising at least one of the previously disclosed compounds and a pharmaceutically acceptable carrier, excipient or diluent.

Some embodiments disclosed include a kit comprising at least one of the previously disclosed compounds. In some embodiments the kit is used for the imaging of CCK2 receptor expressing cells. In another embodiment the cells are tumor or cancer cells. In yet another embodiment the tumor or cancer is selected from the group consisting of kidney cancers, medullary thyroid cancers, insulinomas, small cell lung cancers, bronchial, and ileal carcinoids, GIST tumors, and colon cancers, hepatocellular carcinomas, and pancreatic cancers.

In some embodiments the kit further comprises a derivative of the compound.

In another aspect of the invention, this disclosure provides a method of synthesizing CCK2 receptor-targeted NIR dye conjugates.

In one embodiment, this disclosure provides a method for synthesizing an intermediate of D-CCK2 Ligands (11) having the formula

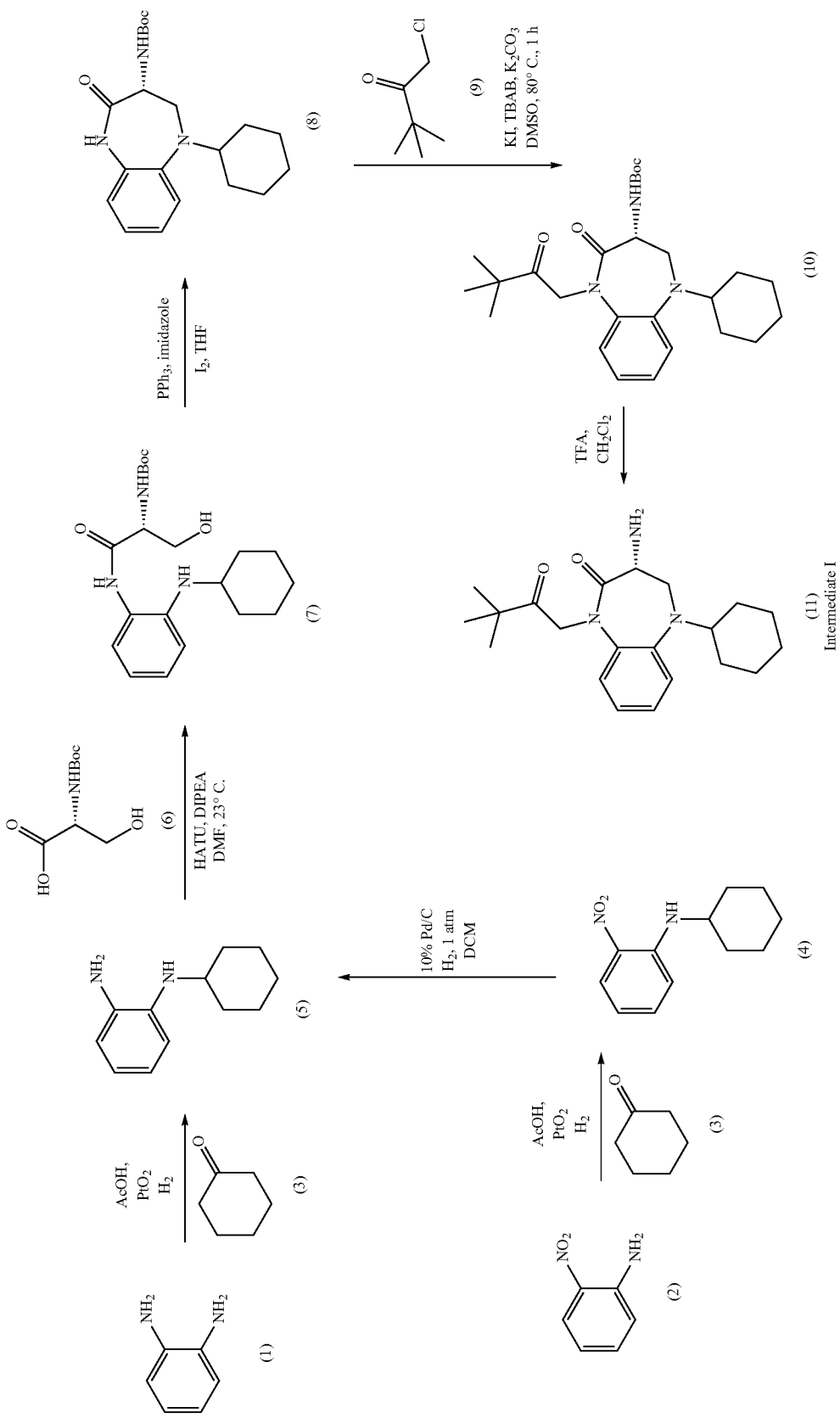

In a second embodiment, this disclosure provides a method for synthesizing an intermediate of D-CCK2 Ligands (11) having the formula

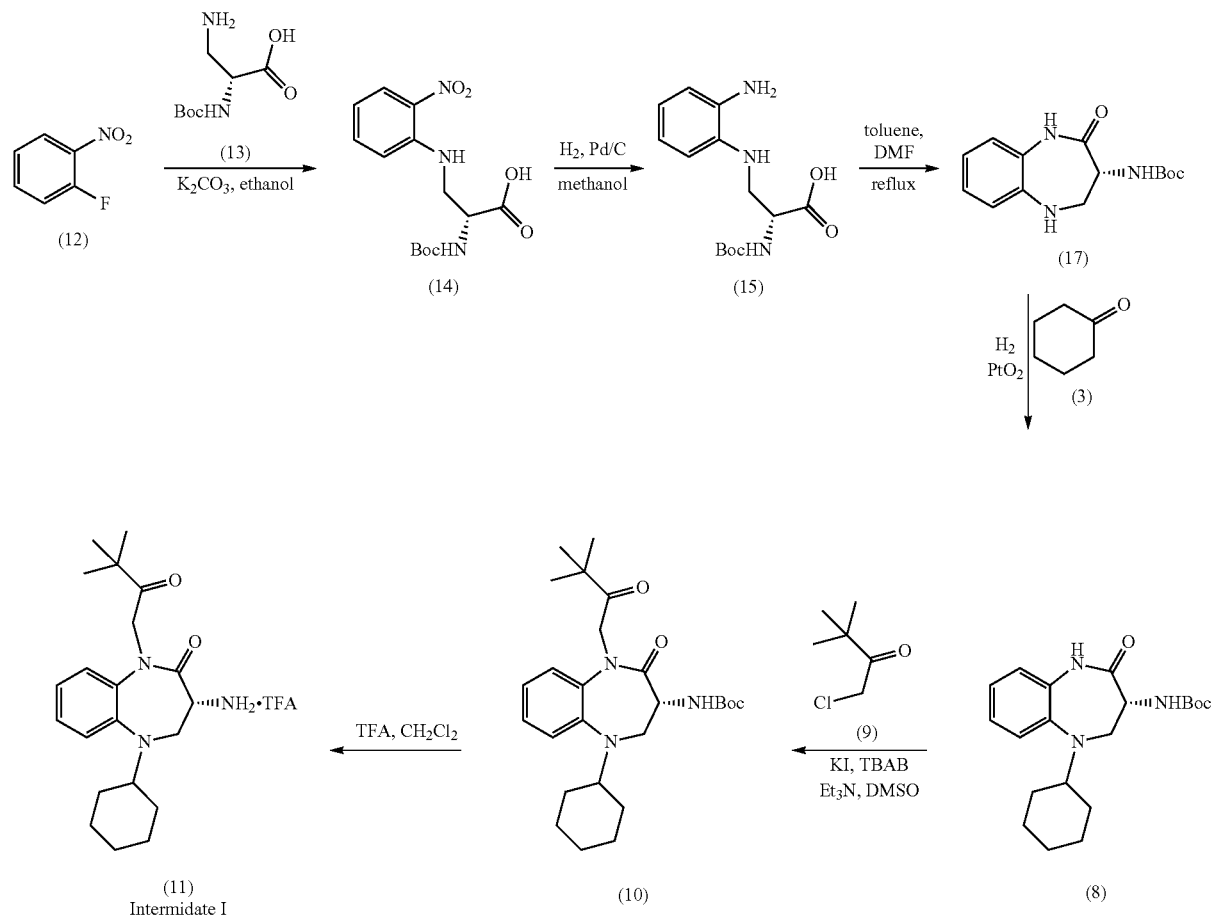

In a third embodiment, this disclosure provides a method for synthesizing a D-CCK2 Ligand 19 having the formula

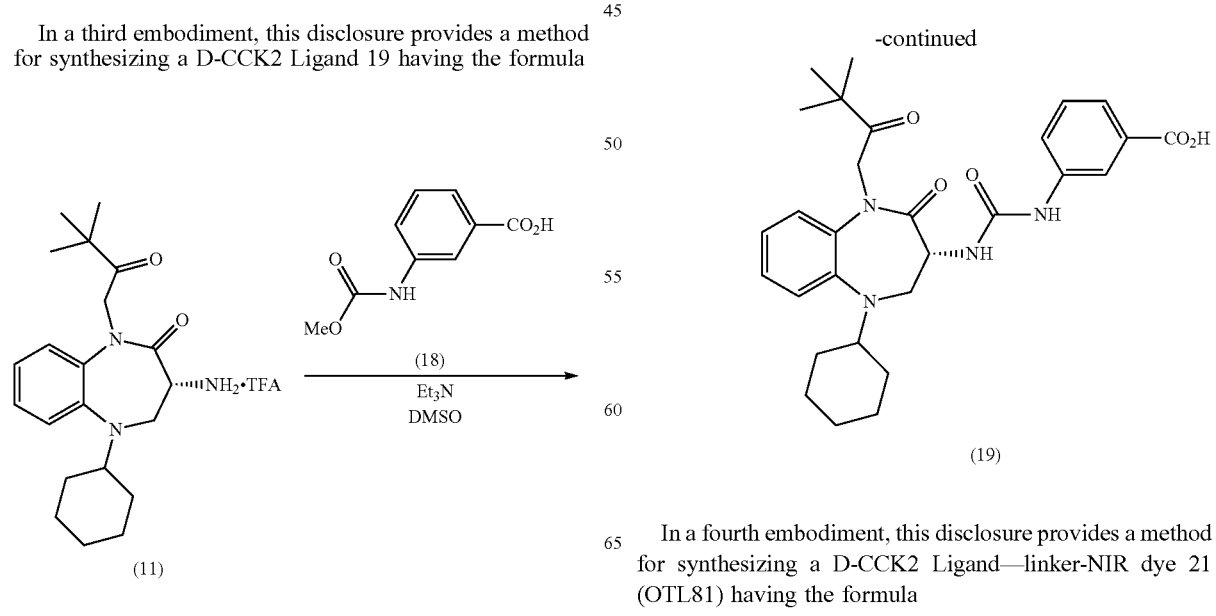

In a fourth embodiment, this disclosure provides a method for synthesizing a D-CCK2 Ligand—linker-NIR dye 21 (OTL81) having the formula

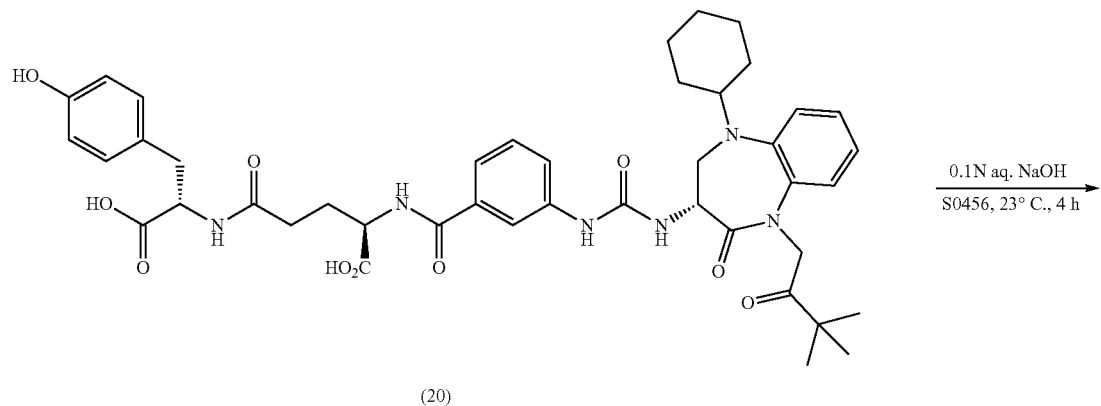
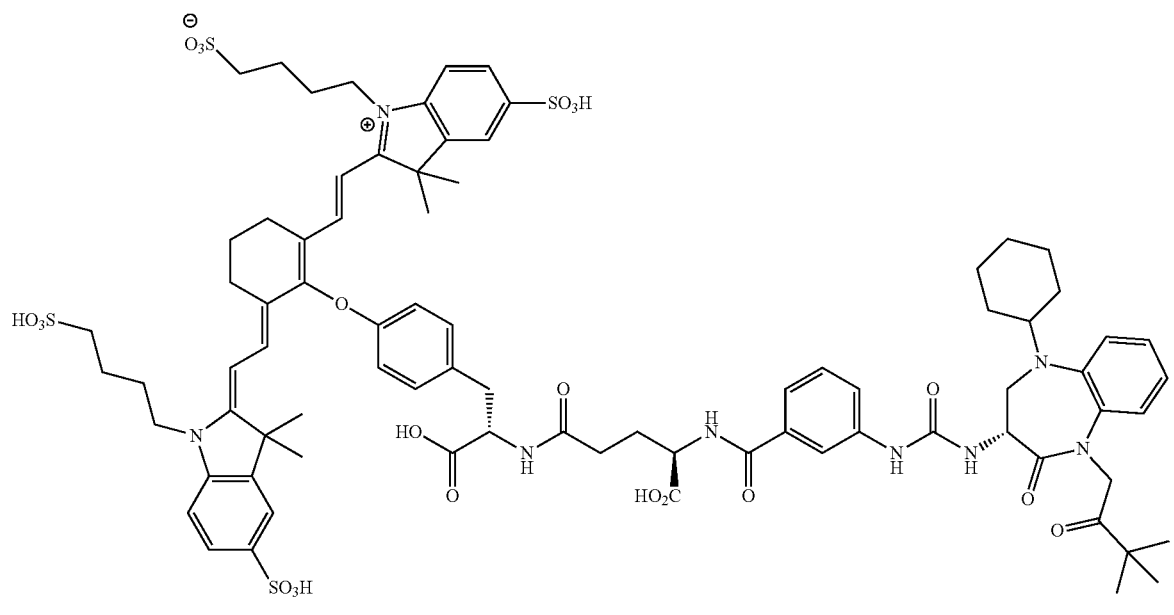
In a fifth embodiment, this disclosure provides a method for synthesizing a D-CCK2 Ligand—linker-NIR dye 29 having the formula
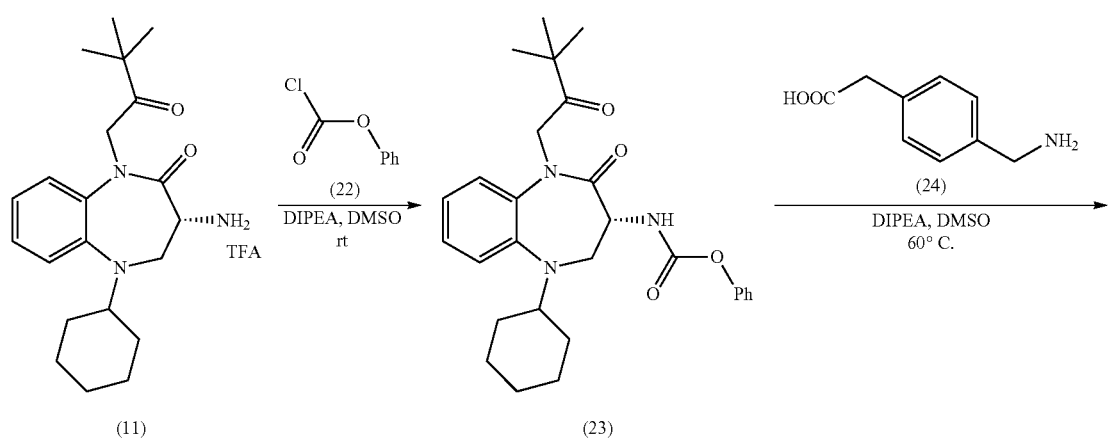

-continued
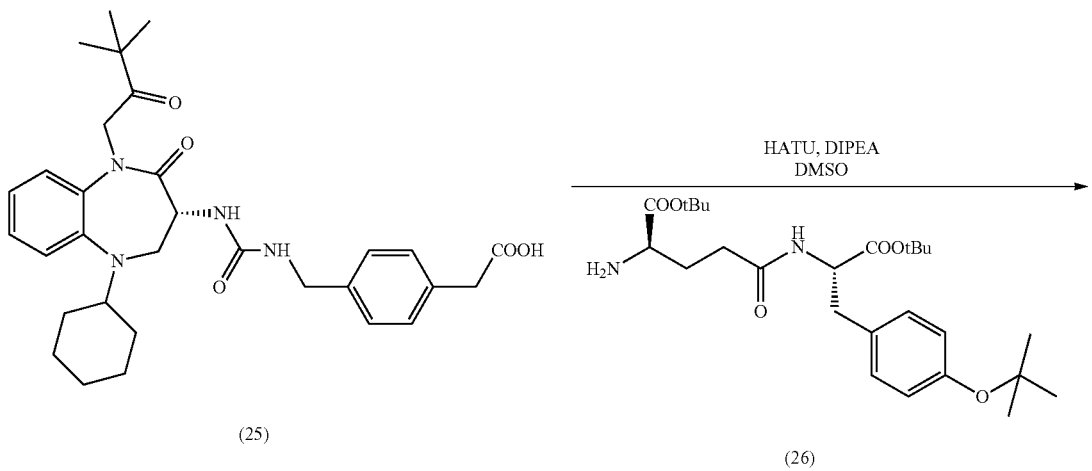
(25) (26)
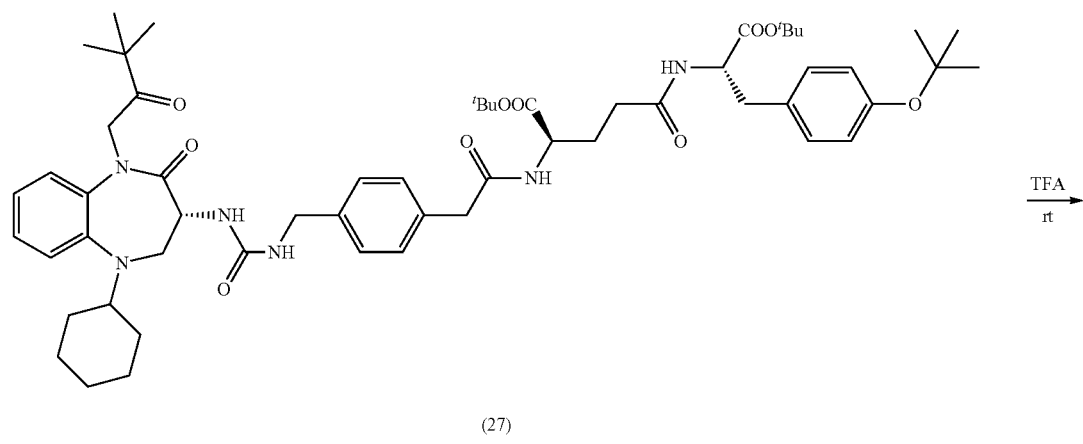
(27)
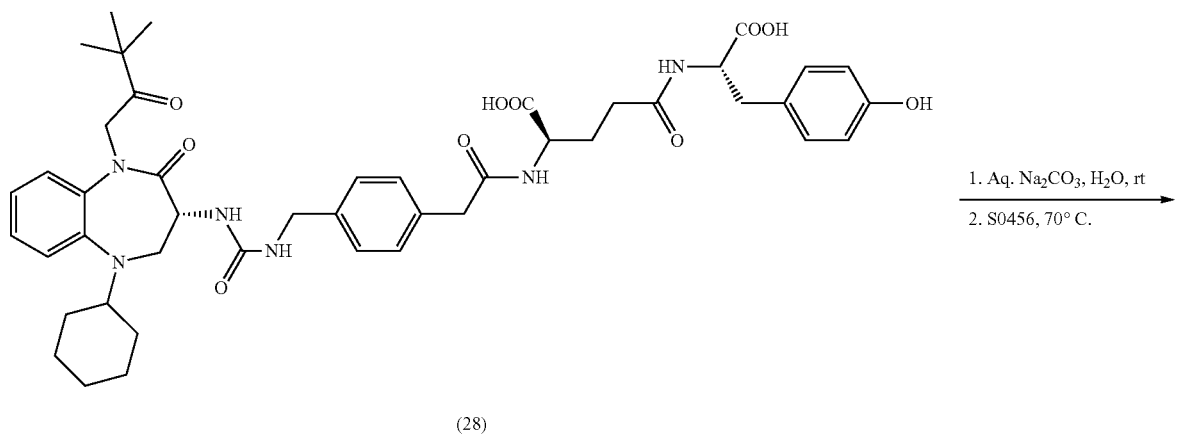
(28)

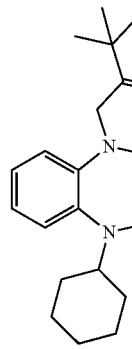
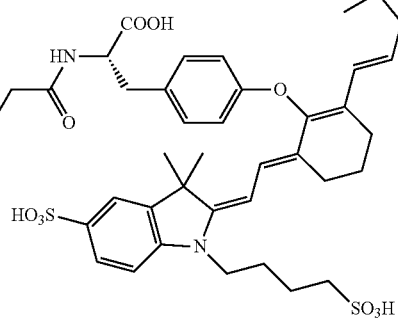
(29)
In a sixth embodiment, this disclosure provides a method for synthesizing a D-CCK2 Ligand—linker-NIR dye 34 having the formula
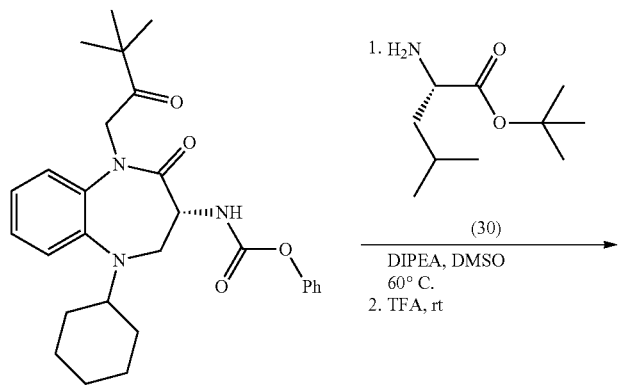
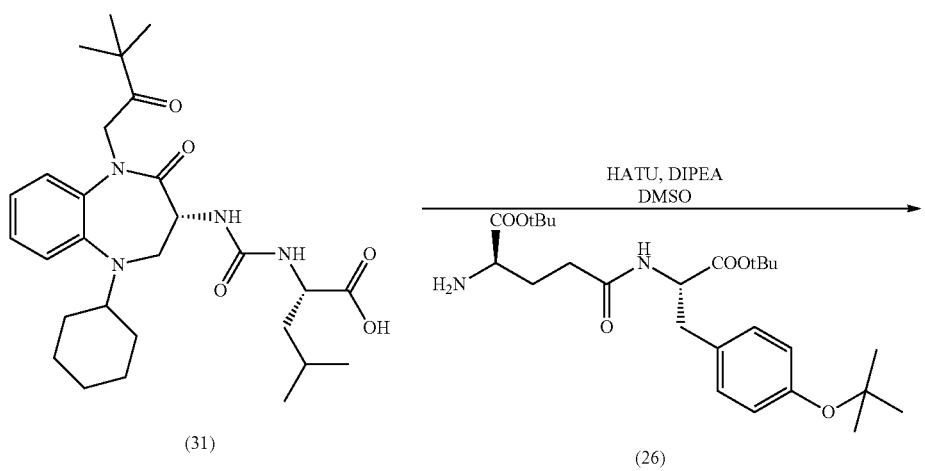

-continued
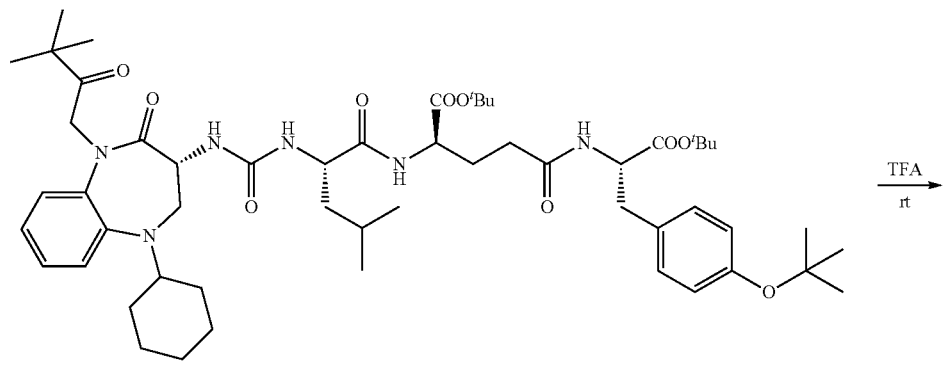
(32) → TFA, rt
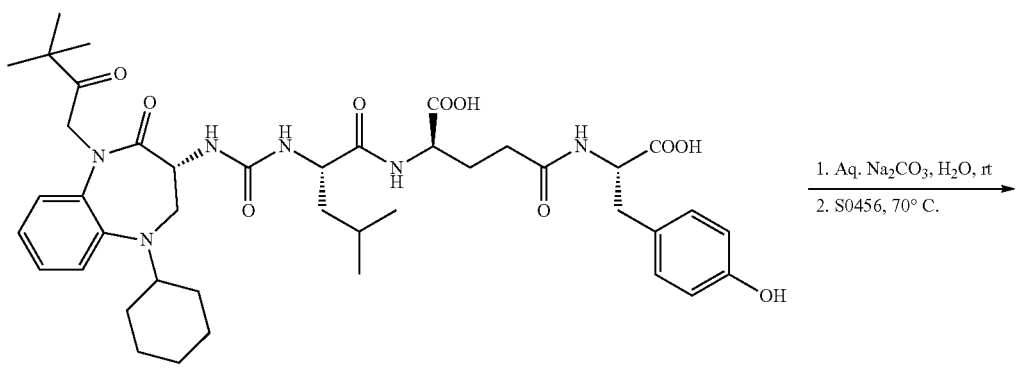
(33) → 1. Aq. Na$_2$CO$_3$, H$_2$O, rt
2. S0456, 70° C.
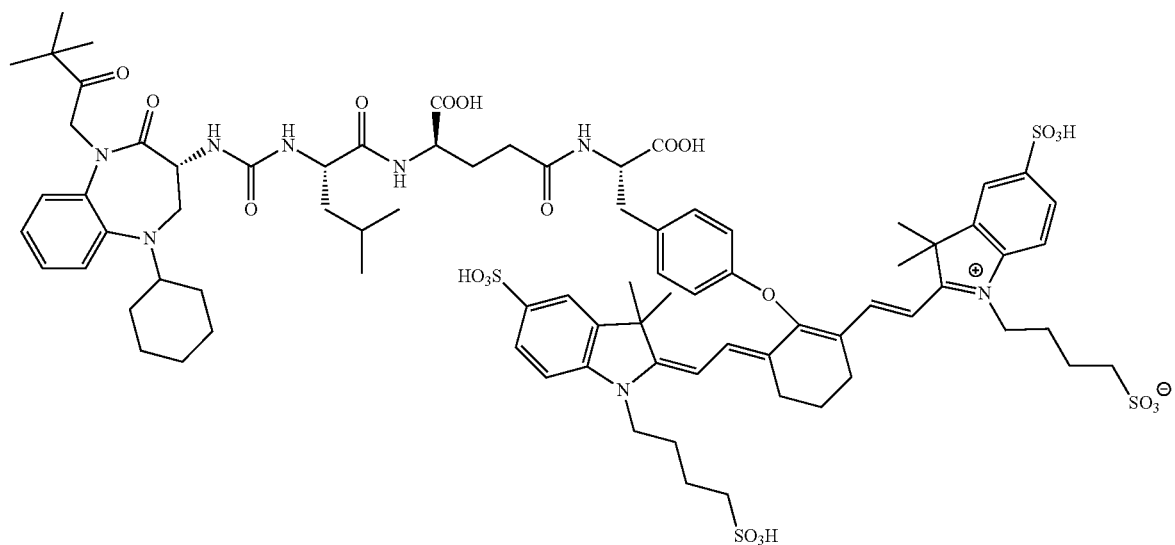
(34)

In a seventh embodiment, this disclosure provides a method for synthesizing a D-CCK2 Ligand—linker-NIR dye 39 having the formula
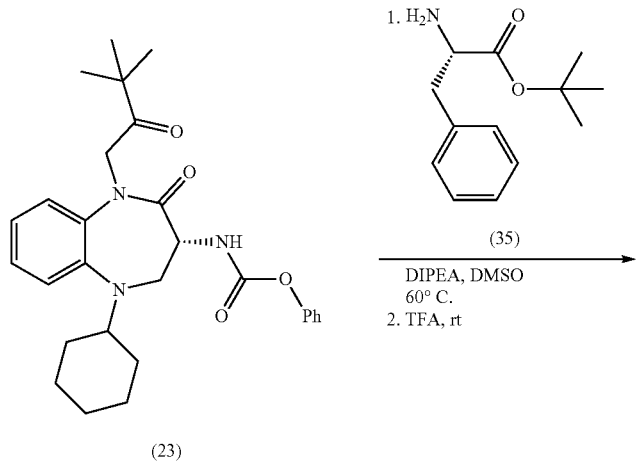
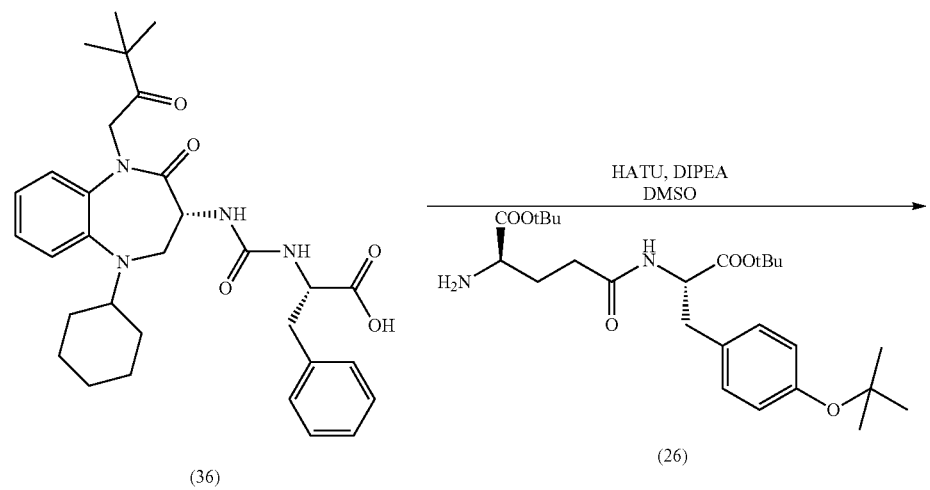
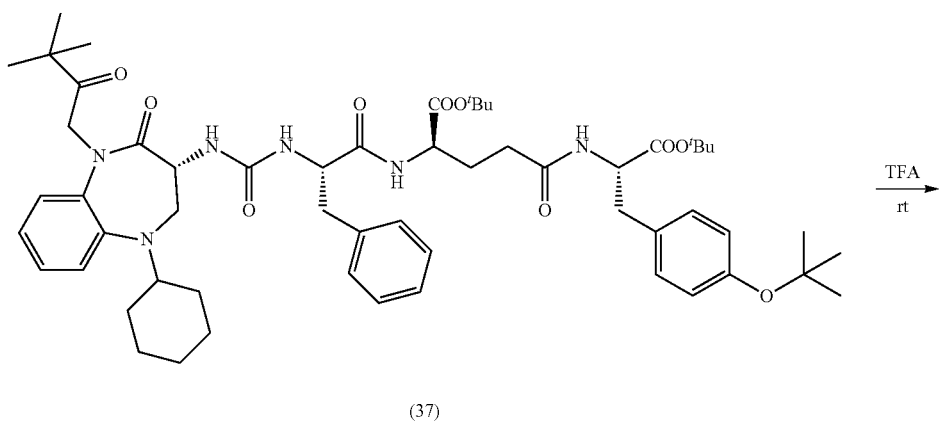

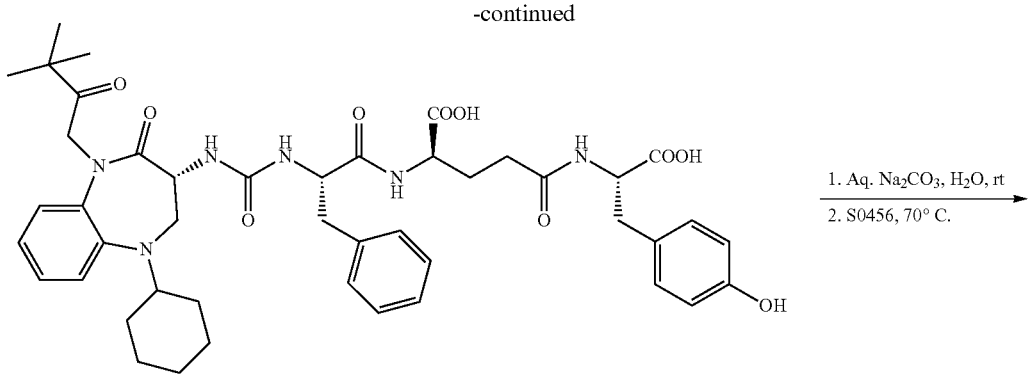

(38)

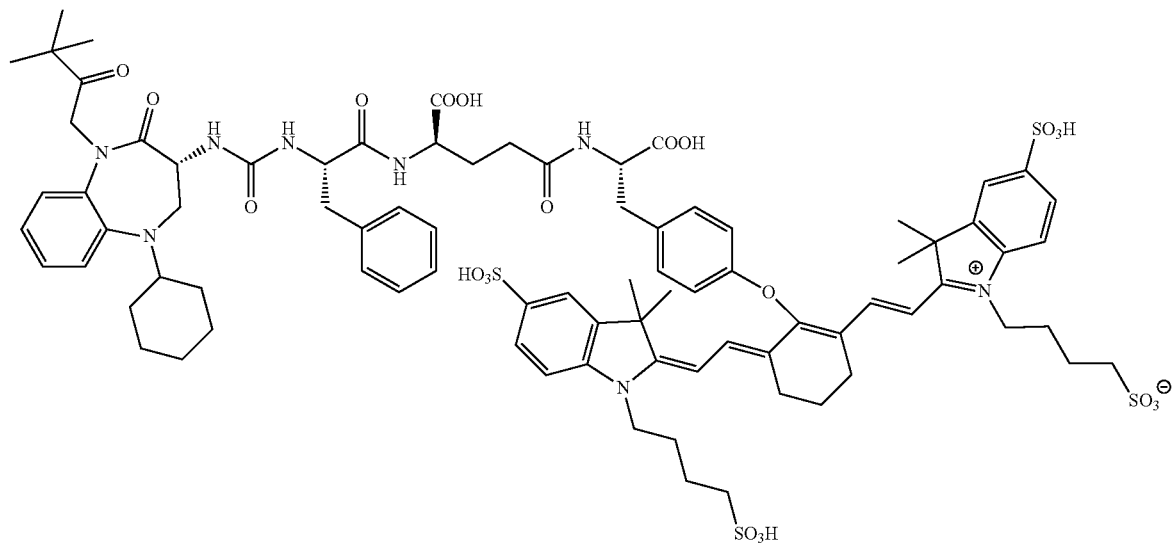

(39)

In another aspect of the invention, this disclosure provides a method of synthesizing N1-cyclohexylbenzene-1,2-diamine (5) having the formula

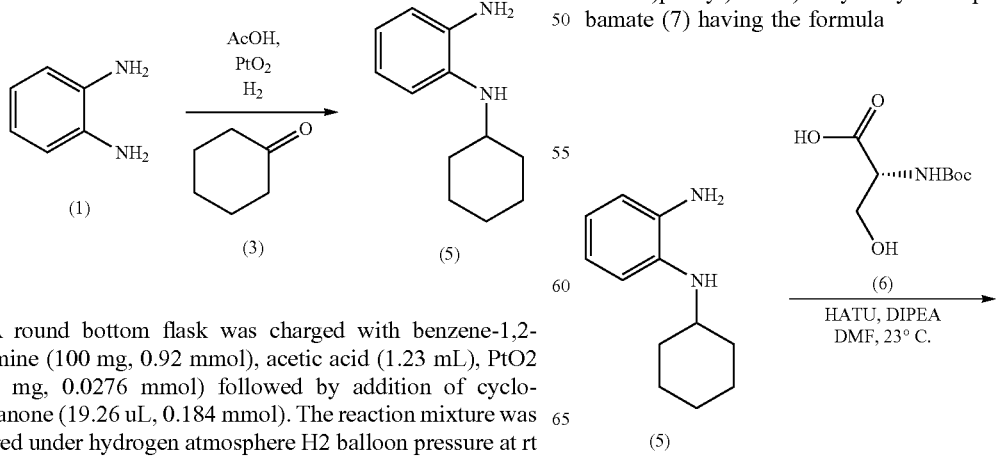

A round bottom flask was charged with benzene-1,2-diamine (100 mg, 0.92 mmol), acetic acid (1.23 mL), PtO2 (6.3 mg, 0.0276 mmol) followed by addition of cyclohexanone (19.26 uL, 0.184 mmol). The reaction mixture was stirred under hydrogen atmosphere H2 balloon pressure at rt for 16 h. Filtered through celite bed and washed with DCM. Evaporated solvent and purified using silica column chromatography to obtain the desired product in 71% yield.

In another aspect of the invention, this disclosure provides a method of synthesizing tert-butyl (R)-(1-((2-(cyclohexylamino)phenyl)amino)-3-hydroxy-1-oxopropan-2-yl)carbamate (7) having the formula -continued

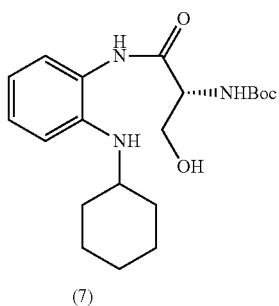

(7)

A round bottom flask was charged with (tert-butoxycarbonyl)-D-serine (108.2 mg, 0.525 mmol), HATU (200 mg, 0.525 mmol), DIPEA (0.184 MI, 1.05 mmol) and DMF (3.25 mL) and stirred for 5 min followed by addition of N1-cyclohexylbenzene-1,2-diamine (100 mg, 0.525 mmol). Continued stirring for 1 h. Reaction mixture was diluted with water and extracted using EtOAc (3×20 mL) and washed with brine. Solvent was evaporated and the crude was purified using silica column chromatography eluting with EtOAc/Hexane to obtain the desired product in 92% yield.

In another aspect of the invention, this disclosure provides a method of synthesizing (R)-3-amino-5-cyclohexyl-1-(3,3-dimethyl-2-oxobutyl)-1,3,4,5-tetrahydro-2H-benzo[b][1,4]diazepin-2-one (11) having the formula

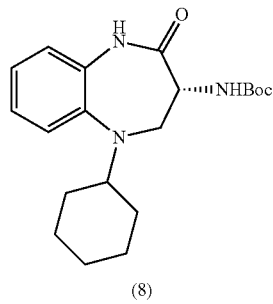

(8)

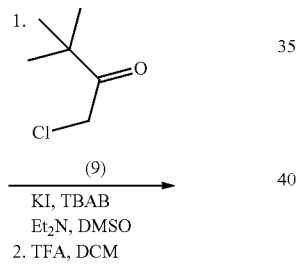

(9)

KI, TBAB
Et₂N, DMSO
2. TFA, DCM

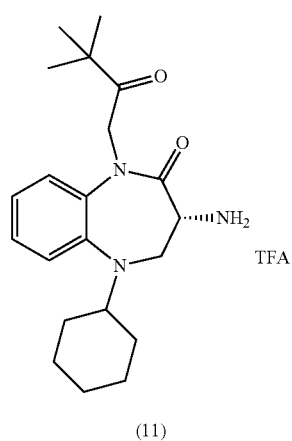

(11)

(R)-3-amino-5-cyclohexyl-1-(3,3-dimethyl-2-oxobutyl)-1,3,4,5-tetrahydro-2H-benzo[b][1,4]diazepin-2-one was prepared using the similar procedure as that of (S)-3-amino-5-cyclohexyl-1-(3,3-dimethyl-2-oxobutyl)-1,3,4,5-tetrahydro-2H-benzo[b][1,4]diazepin-2-one In another aspect of the invention, this disclosure provides a method of synthesizing (R)-3-(3-(5-cyclohexyl-1-(3,3-dimethyl-2-oxobutyl)-2-oxo-2,3,4,5-tetrahydro-1H-benzo[b][1,4]diazepin-3-yl)ureido)benzoic acid (19) having the formula

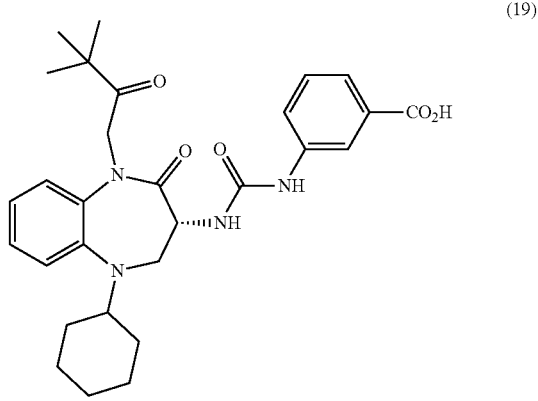 [SMILES: CC(C)(C)C(=O)CN1C(=O)[C@H](NC(=O)Nc2cccc(C(=O)O)c2)CN(C2CCCCC2)c2ccccc21]

(19)

Synthesis of (R)-3-(3-(5-cyclohexyl-1-(3,3-dimethyl-2-oxobutyl)-2-oxo-2,3,4,5-tetrahydro-1H-benzo[b][1,4]diazepin-3-yl)ureido)benzoic acid was achieved starting with (R)-3-amino-2-((tert-butoxycarbonyl)amino)propanoic acid using the similar synthetic procedures as that of (S)-3-(3-(5-cyclohexyl-1-(3,3-dimethyl-2-oxobutyl)-2-oxo-2,3,4,5-tetrahydro-1H-benzo[b][1,4]diazepin-3-yl)ureido)benzoic acid In another aspect of the invention, this disclosure provides a method of synthesizing 4-(2-((E)-2-((E)-2-(4-((S)-2-carboxy-2-((R)-4-carboxy-4-(3-(3-((R)-5-cyclohexyl-1-(3,3-dimethyl-2-oxobutyl)-2-oxo-2,3,4,5-tetrahydro-1H-benzo[b][1,4]diazepin-3-yl)ureido)benzamido)butanamido)ethyl)phenoxy)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate (21) having the formula

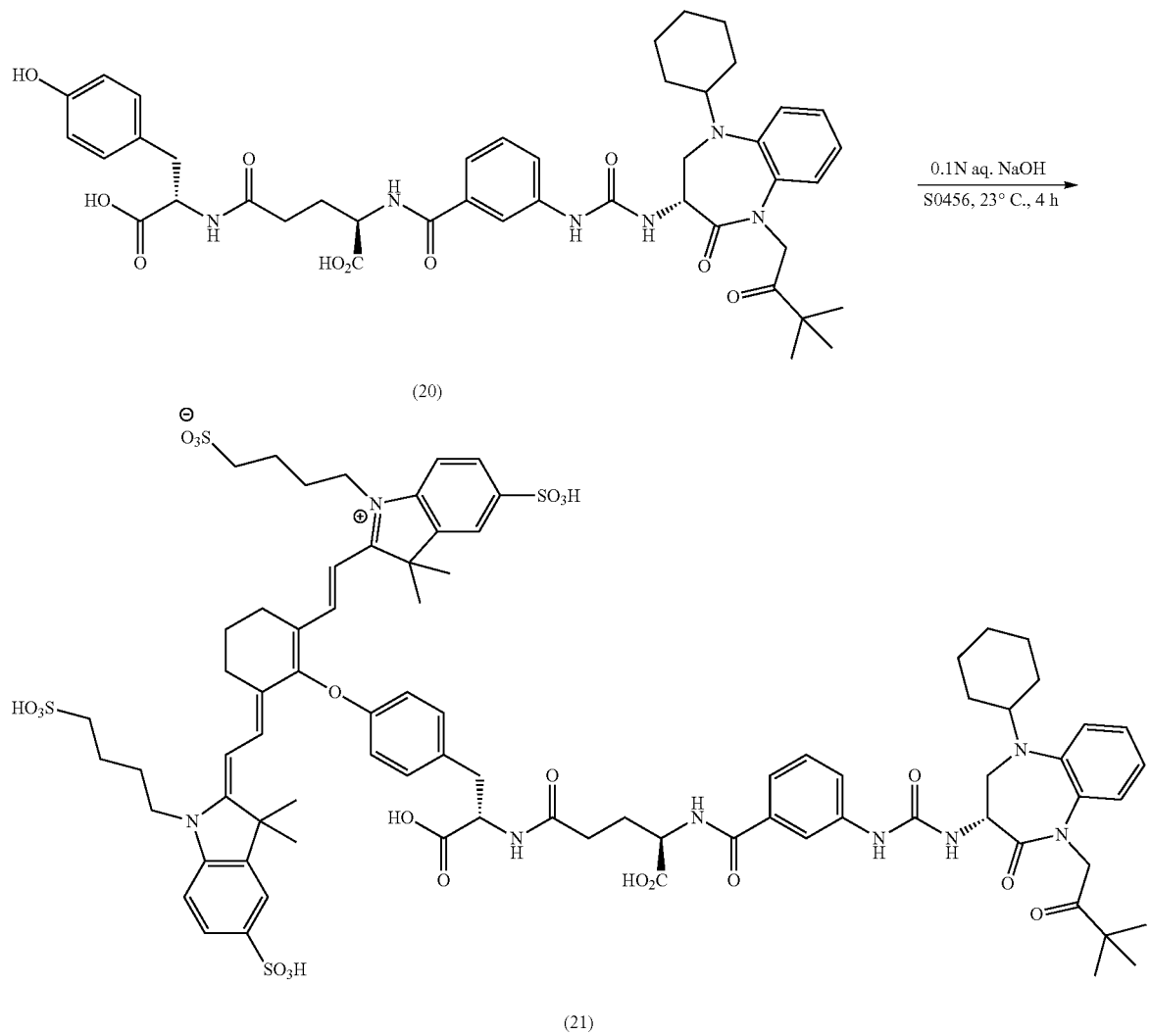

4-(2-((E)-2-((E)-2-(4-((S)-2-carboxy-2-((R)-4-carboxy-4-(3-(3-((R)-5-cyclohexyl-1-(3,3-dimethyl-2-oxobutyl)-2-oxo-2,3,4,5-tetrahydro-1H-benzo[b][1,4]diazepin-3-yl)ureido)benzamido)butanamido)ethyl)phenoxy)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate was prepared using the similar protocol as that of 4-(2-((E)-2-((E)-2-(4-((S)-2-carboxy-2-((R)-4-carboxy-4-(3-(3-((S)-5-cyclohexyl-1-(3,3-dimethyl-2-oxobutyl)-2-oxo-2,3,4,5-tetrahydro-1H-benzo[b][1,4]diazepin-3-yl)ureido)benzamido)butanamido)ethyl)phenoxy)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate The remaining CCK2 receptor-targeted NIR conjugates disclosed were synthesized following similar synthesis schemes and synthesis procedures.

III. Methods of Detection, Diagnosis and Imaging

The present invention also includes methods of using the compounds in a variety of applications, such as in methods of detecting, diagnosing and imaging cancer. For example, in one aspect the invention is directed to methods for detecting a tumor in a subject, comprising administering compounds as defined herein to a subject suspected of having a tumor and detecting the compounds in the subject, wherein the active moiety Z of the compounds is an optical imaging agent. In a related aspect, the invention includes methods for diagnosing cancer in a subject, comprising administering compounds as defined herein to a subject suspected of having cancer and detecting the compounds in the subject, wherein the active moiety Z of the compounds is an imaging agent. In a further related aspect, the invention includes methods for imaging cancer in a subject, comprising administering compounds as defined herein to a subject suspected of or having cancer and detecting the compounds in the subject, wherein the active moiety Z of the compounds is an imaging agent.

IV. Pharmaceutical Formulations

The methods of the present invention using the compounds may be practiced in one or more of in vitro, in vivo and ex vivo applications. When used in vivo and ex vivo, the compounds may be prepared as a pharmaceutical composition comprising the compounds and one or more pharmaceutically-acceptable carriers and/or diluents. The skilled artisan will understand that the specific elements comprising a pharmaceutical composition will depend on factors that include the identity of the targeting ligand and the active moiety in the compounds, the identity of the cancer or tumor to be detected or treated, the location in the subject of the cancer or tumor, available means for detecting the imaging agent, and the means used to administer the compounds to the subject.

The pharmaceutical compositions of the present invention may be formulated, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of pharmaceutical compositions can be used to effect such administration.

Examples of parenteral dosage forms include aqueous solutions of the compounds, in an isotonic saline, 5% glucose or other well-known pharmaceutically-acceptable liquid carriers such as liquid alcohols, glycols, esters, and amides. The parenteral dosage form in accordance with this invention can be in the form of a reconstitutable lyophilizate comprising the dose of the compounds. In one aspect of the present embodiment, the compounds may be formulated into prolonged or extended release formulations such as, for example, the biodegradable carbohydrate matrices described in U.S. Pat. Nos. 4,713,249, 5,266,333, and 5,417,982, the disclosures of each of which are incorporated herein by reference in their entireties, or alternatively, a slow pump (e.g., an osmotic pump) can be used.

In one aspect on the invention, at least one additional therapeutic factor can be administered to a subject in combination with or as an adjuvant to the compounds and methods of the present invention to enhance the compounds-mediated elimination of the population of pathogenic cells, or more than one therapeutic factor can be used. In one example, the therapeutic factor can be selected from a chemotherapeutic agent, or another therapeutic factor capable of complementing the efficacy of the administered compounds of the present invention. In another example, chemotherapeutic agents which are, for example, cytotoxic themselves, can work to enhance tumor permeability, are also suitable for use as an additional therapeutic factor.

The therapeutic factor can be administered to the subject prior to, after, or at the same time as the compounds, and the therapeutic factor can be administered as part of the same composition containing the compounds or as part of a different composition than the compounds. Any such therapeutic composition containing the therapeutic factor at a therapeutically effective dose can be used in the present invention.

VI. Administration to Subjects

A. Methods of Detection, Diagnosis and Imaging

The amount of compounds used in the methods of detection, diagnosis and imaging described herein will also depend on a variety of factors, including the identity of the targeting ligand, the identity of the imaging agent, the identity of the cancer or tumor to be detected, the location in the subject of the cancer or tumor, available means for detecting the imaging agent, and the means used to administer the compounds to the subject.

The skilled artisan will understand that each of the methods of detection, diagnosis and imaging can be practiced using one type of compounds, or more than one type of compounds, such as two, three, four or more. When two or more types of compounds are used, the methods can be practiced by administering two or more types compounds to the subject concurrently or sequentially, separated in time by 5, 10, 15, 20, 25, 30 or more minutes, depending on the method being practiced. Illustratively, for example, the subject can be administered compounds with different targeting ligands, but the same active moiety in a co-dosing protocol. In other embodiments, the subject can be administered compounds comprising the same targeting ligand linked to different active moieties, or different targeting ligand linked to different active moieties.

When used in methods of detection, diagnosis and imaging, the compounds are preferably administered to a subject parenterally, e.g., intradermally, subcutaneously, intramuscularly, intraperitoneally, intravenously, or intrathecally. However, the skilled artisan will understand that in some instances, administration may be oral, sublingual, intranasal, intraocular, rectal, transdermal, mucosal, pulmonary, or topical.

In addition to detecting the compounds, the skilled artisan will understand that the amount of signal detected can be compared to other values, such as control values from a subject known to not have a tumor or cancer, or values obtained on an earlier date from the same subject. Thus, each of the methods of the present invention may alternatively comprise measuring the amount of compounds in the subject, rather than simply detecting it, and optionally further comparing the measured amount to a control value or a value obtained at an earlier time in the same subject.

The means used to detect the compounds vary based on factors including the identity of the imaging agent, whether the method is being practiced in vitro, in vivo or ex vivo, and when practiced in vivo, the location in the subject to be visualized.

VII. Examples

General Methods:

HEK-CCK2 cells (a human embryonic kidney cells transfected with CCK2 receptor) were a kind gift from Dr. Mark Hellmich (University of Texas Medical Branch, Galveston, Tex.) and grown as a monolayer using Dulbecco's Modified Eagles Medium (GIBCO) (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude (nu/nu) mice (5 weeks old, 18-20 g) were purchased from Envigo (Indianapolis, Ind.) and maintained on normal rodent diet (Teklad, Wis.). Animals were housed 5/cage in a barrier, pathogen-free cloaked rack. Autoclaved tap water and food were given as needed. The animals were housed in a sterile environment on a standard 12 hour light-dark cycle for the duration of the study. Mice were identified individually by ear punch. All animal procedures were approved by Purdue Animal Care and Use Committee. Animal care and studies were performed according to national and international guidelines for the humane treatment of animals.

In Vitro Binding and Specificity:

HEK cells that overexpress CCK2 were seeded into a T75 flask and allowed to form a monolayer over 48 h. After trypsin digestion, release cells were transferred into centrifuge tubes (1×10⁶ cells/tube) and centrifuged. The medium was replaced with fresh medium containing increasing concentration of requisite CCK2R-Ligand-NIR dye compound in the presence or absence of 100-fold excess the ligand, a high affinity CCK2 receptor antagonist, and incubated for 1 h at 37° C. After rinsing with fresh medium (2×1.0 mL) and PBS (1×1.0 mL), cells were resuspended in PBS (1.0 mL) and cell bound fluorescence was analyzed (100,000 cells/sample) using a fluorometer (Cary, Agilent). The relative binding affinities were calculated using a plot of % cell bound fluorescence versus the log concentration of the test article using GraphPad Prism 4.

Whole-Body Imaging:

six-weeks-old female nu/nu mice were inoculated subcutaneously with HEK-CCK2 cells (5.0×10⁶/mouse in 50% high concentrated matrigel in GIBCO medium) on the shoulder. Growth of the tumors was measured in perpendicular directions every 2 days using a caliper (body weights were monitored on the same schedule), and the volumes of the tumors were calculated as 0.5×L×W² (L=longest axis and W=axis perpendicular to L in millimeters). Once tumors reached between 400 mm³ in volume, animals (5 mice/group) were intravenously injected with 10 nmol of requisite CCK2R-Ligand-NIR dye compounds in phosphate buffered saline (100 µL). For whole body imaging and biodistribution studies, animals were euthanized by $CO_2$ asphyxiation 2 hours after administration of the compound of interest.

whole-body imaging (intact tumor) experiments were then performed using a Caliper IVIS Lumina II Imaging Station with Living Image 4.0 software (PerkinElmer Inc, MA).

Settings for imaging:—lamp level: medium; excitation: 745 nm; emission: ICG (830 nm); epi illumination; binning: 4 (M), FOV=12.5; f-stop=2; acquisition time=1 s. For time dependent studies, animals were imaged under anesthesia using isoflurane. Whole body imaging (intact tumor) experiments was then performed using a Caliper IVIS Lumina II Imaging Station with Living Image 4.0 software (PerkinElmer Inc, MA).

Tissue Bio-Distribution:

Following Whole-body imaging, animals were dissected and selected tissues (heart, lung, liver, spleen, kidneys, stomach, small intestine, large intestine, muscle, skin, and tumor) were analyzed for fluorescence activity using IVIS imager as before. Settings for imaging:—lamp level: medium; excitation: 745 nm; emission: ICG; epi illumination; binning: 4 (M), FOV=12.5; f-stop=2; acquisition time=1 s.

Example 1: Pre-Clinical Evaluations of CCK2R-Targeted NIR Compounds with a Single Amino Acid Spacer Conclusion of In Vivo Studies:

Difference between the compounds 40 and 41 is, the compound 41 has extra benzyl residue between the tyrosine and urea moiety. The compounds 41 showed a higher specificity, higher accumulation, fast skin clearance when compared to the compound 40 indicating that extra benzyl residue in the compounds 41 play role in the receptor binding, specificity, and pharmacokinetic properties of the final compounds.

Example 2: Pre-Clinical Evaluations of CCK2R-Targeted NIR Compounds with a Short Amino Acid Spacers In Vitro Studies:

TABLE 1

Binding affinity of CCK2R-NIR compounds 2-6 to CCK2R-positive HEK-CCK2R cancer cells.

| Compound | $K_D$ (nM) |
|---|---|
| (21) | 0.67 |
| (42) | 1.74 |
| (43) | 0.81 |
| (44) | 2.6 |

Conclusion of In Vitro Studies:

The in vitro binding affinity data showed that the compounds 21 and 43 have very high affinity for CCK2R whereas the compounds 42 and 44 have relatively weaker affinity for CCK2R when compared to 21 and 43. Whole body imaging and biodistribution data demonstrated that all compounds accumulated in the CCK2R-positive tumors. However, the compounds 21 and 41 had very high fluorescence intensity in the tumors indicating high efficacy of those compounds in for CCK2R. Head-to-head comparison of tumor uptake of compounds demonstrated that compounds 21 has the highest tumor uptake in all four tumors indicating it would be a good clinical candidate to use in image-guided surgery for CCK2R-positive cancers.

Example 3: Pre-Clinical Evaluations of CCK2R-Targeted NIR Compounds with a Short Amino Acid Spacers with Chiral Modifications In vitro studies:

TABLE 2

Binding affinity of CCK2R-NIR compounds 45-49 to CCK2R-positive HEK-CCK2R cancer cells.

| Compound | $K_D$ (nM) |
|---|---|
| (45) | 2.3 |
| (46) | 34.03 |
| (47) | 14.74 |
| (48) | 0.90 |
| (49) | 13.90 |

Conclusion of In Vitro Studies:

The in vitro binding affinity data showed that the compound 10 has a very high affinity for CCK2R whereas the compounds 8, 9, and 11 have relatively weak affinity for CCK2R. This may be due to the changing the chirality of the ligand from D-isomer to L-isomer. However, compound 10 has a less affinity for CCK2R compared to compound 21. So, decided to conduct lead optimization around compound 21.

Example 4: Extended Pre-Clinical Evaluations of Compounds 21

Figure 12:
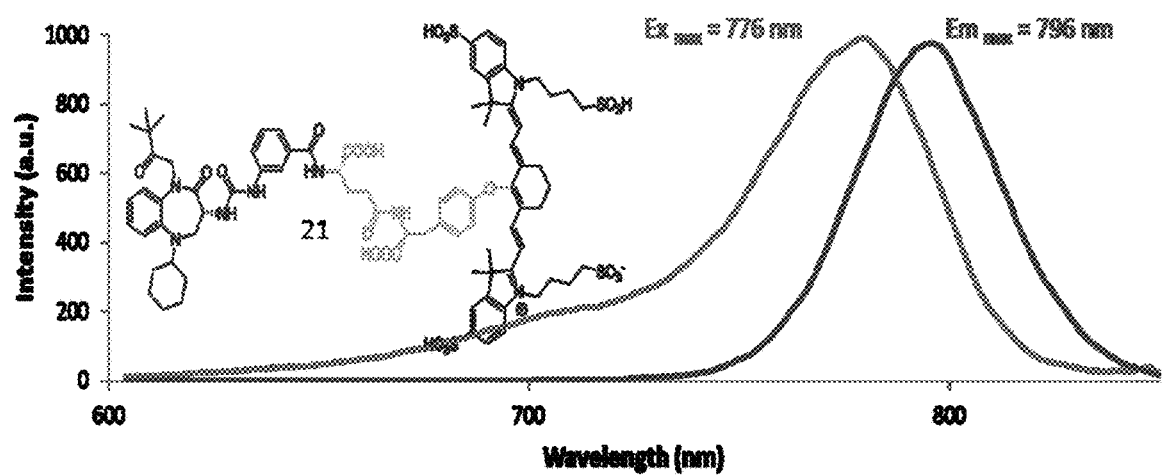
FIG. 12 depicts the chemical structure, excitation and emission spectra of compound 21 (OTL81).
Figure 13:
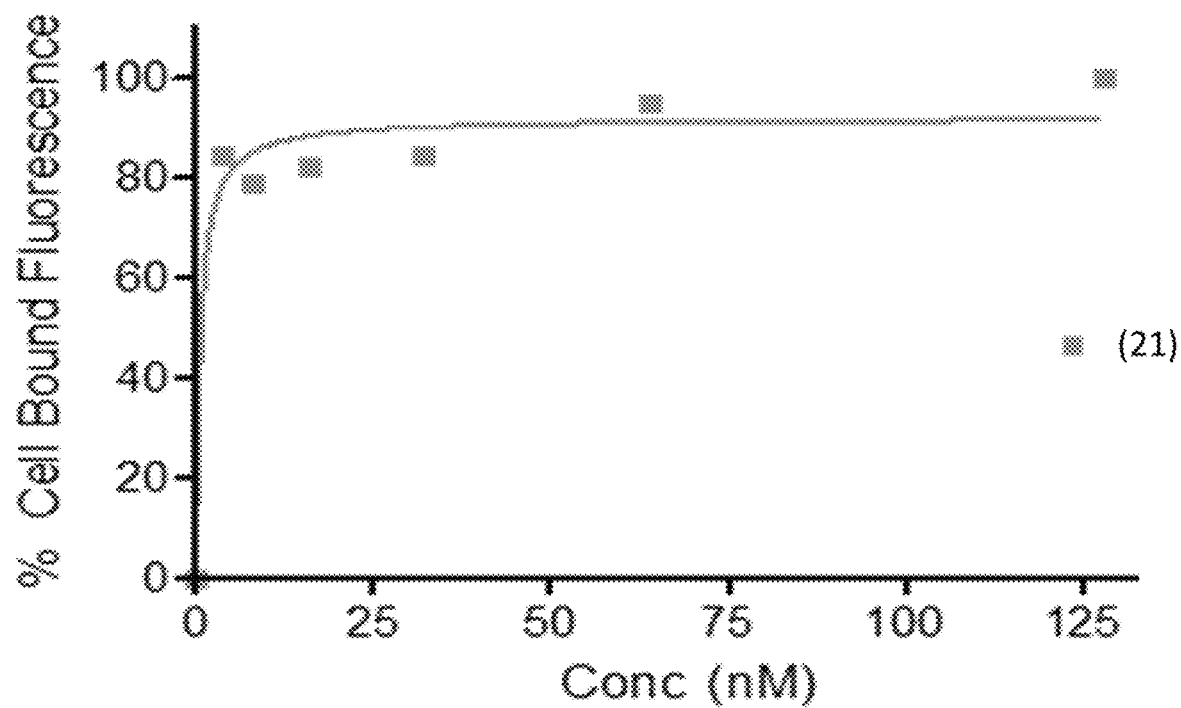
FIG. 13 illustrates the binding affinity of compounds 3 to CCK2R. CCK2R-positive HEK-CCK2R cancer cells were incubated for 1 h at 37° C. with increasing concentrations of compound 21. Media was then removed, washed with fresh media three times, and replaced with PBS. Cell bound fluorescence was assayed as using fluorometer.
Figure 14A:
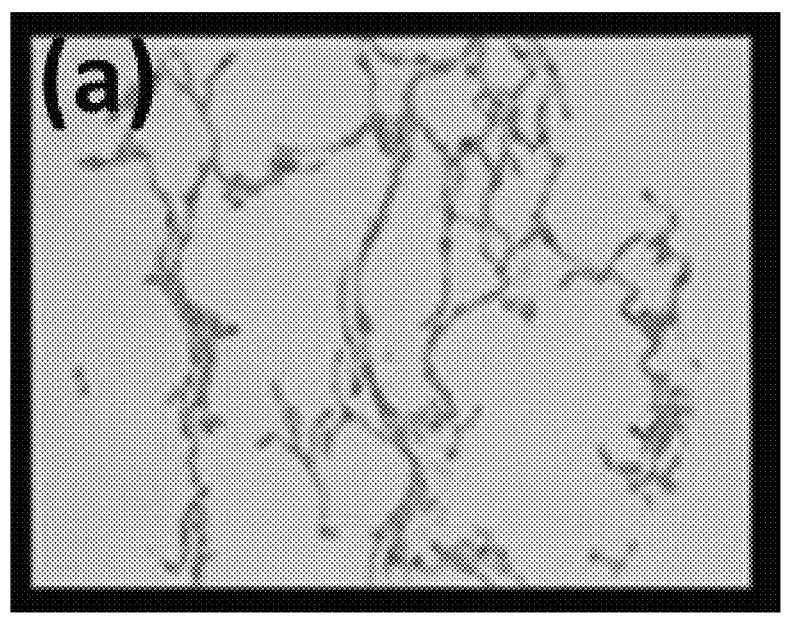
FIG. 14A shows a resected healthy adjacent lung tissue from a lung adenocarcinoma patient which did not express CCK2R.
Figure 14B:
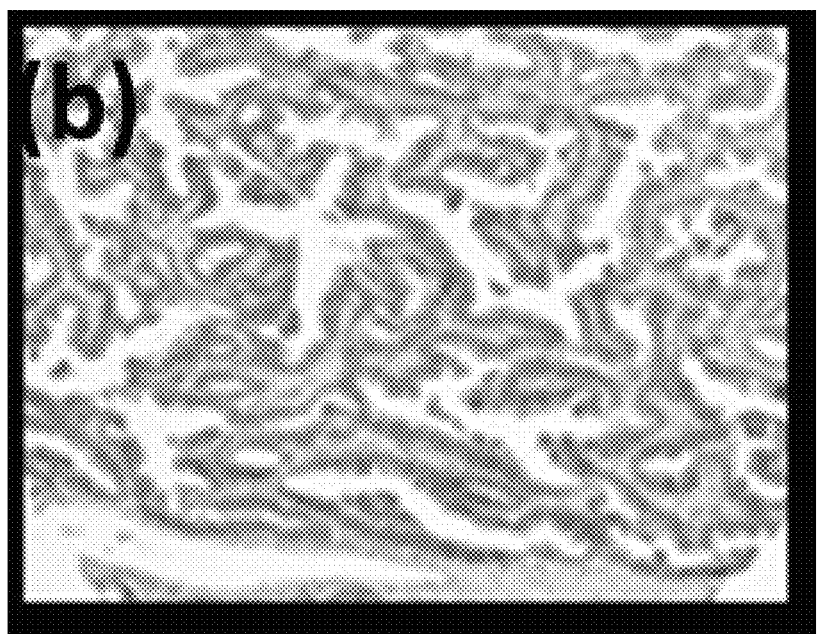
FIG. 14B depicts the stained resected lung adenocarcinoma specimen demonstrates strong CCK2R expression.
Figure 14C:
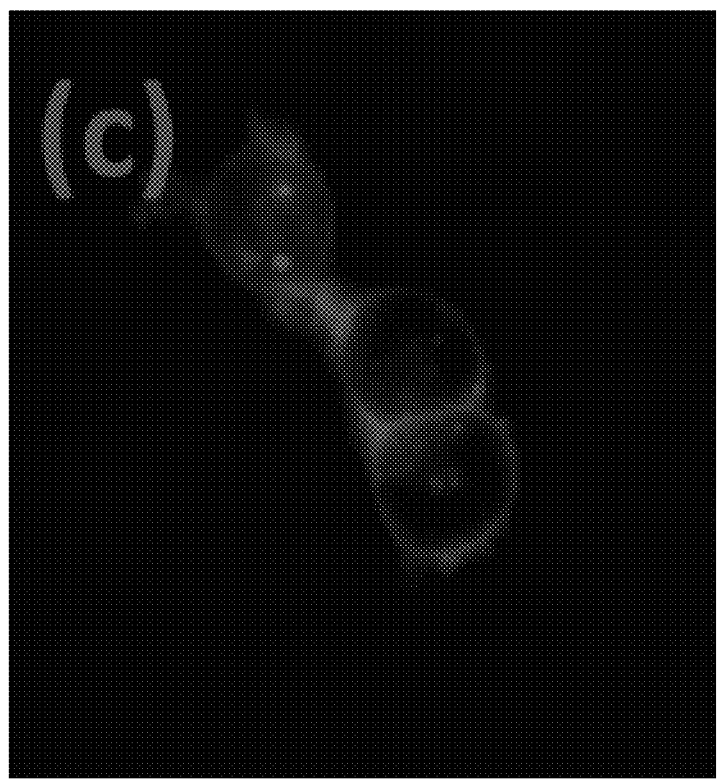
FIG. 14C demonstrates the binding of 21 to CCK2R expressing HEK cells by epi-fluorescence microscopy.
Figure 14D:
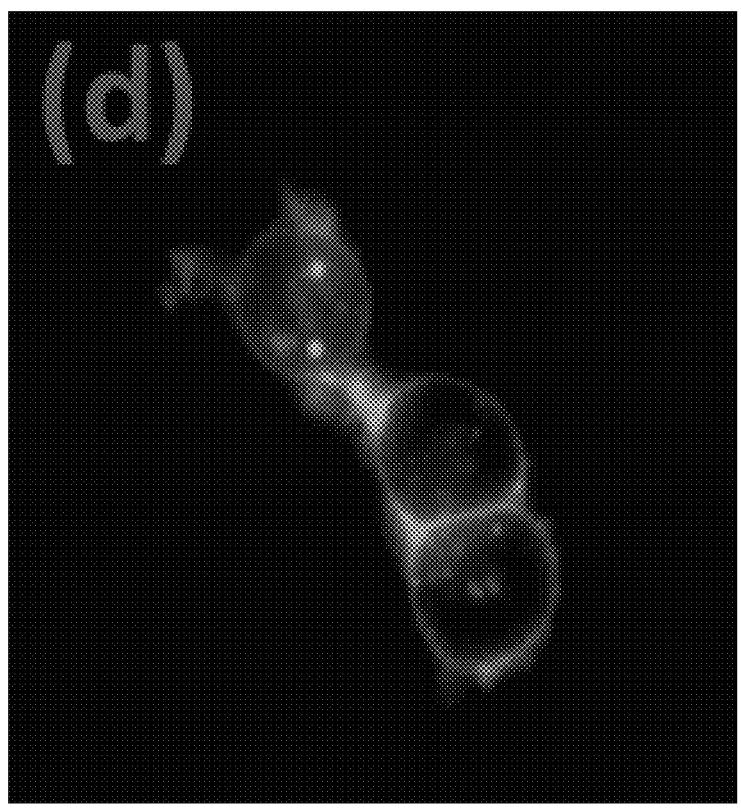
FIG. 14D demonstrates the binding of 21 to CCK2R expressing HEK cells by epi-fluorescence microscopy.
Figure 14E:
FIG. 14E depicts the in vivo efficacy and specificity of 21 by whole-body imaging with nude mice bearing HEK-CCK2R tumors.
Figure 14F:
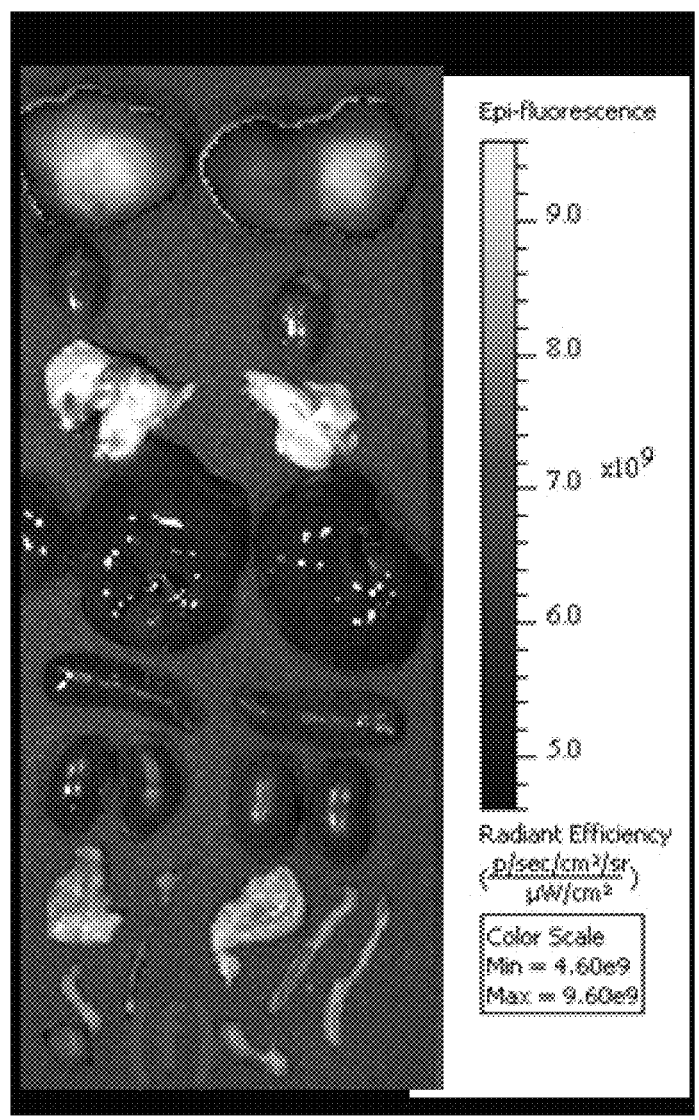
FIG. 14F depicts the ex vivo tissue biodistribution of mice of FIG. 14E dissecting after whole-body imaging.

Conclusion:

The compound 21 is excited at 776 nm and emits at 796 nm (FIG. 12) demonstrating 20 nm Stokes shift with great NIR properties. The dissociation constant ($K_D$) of 3 derived from the studies was calculated to be 1 nM (FIG. 13) indicating very high affinity for CCK2 receptor. The compound 3 was seen to efficiently label HEK-CCK2 cells (FIGS. 14*c* & *d*).). IHC power analysis suggested that over 60% of samples had moderate to strong expression levels of CCK2R whereas healthy lungs did not express CCK2R (FIG. 14*a-b*). Moreover, whole-body imaging with mice bearing HEK-CCK2R tumor xenografts (FIG. 14*c*) and their ex vivo tissue biodistribution (FIG. 14*f*) indicated that the compounds 21 was solely taken up in CCK2R positive tumors with no accumulation in other tissues, demonstrating a very high tumor-to-background ratio.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety.

What is claimed is:

1. A compound having the formula B-L-Z
   wherein B is a targeting ligand capable of selectively binding to CCK2R and/or CCK2i4svR selected from the group consisting of

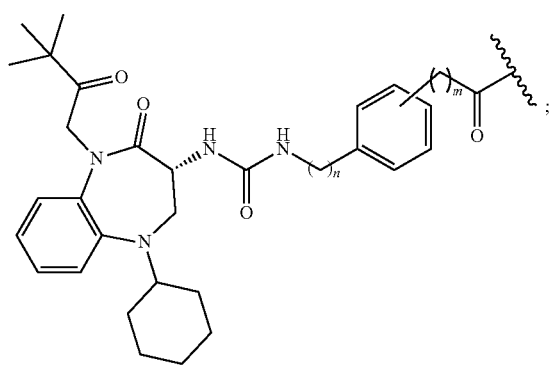

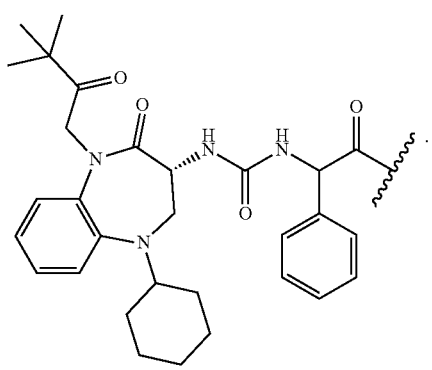

-continued

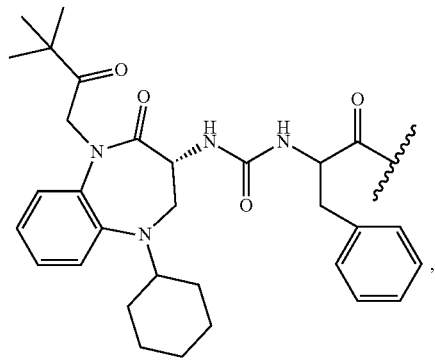

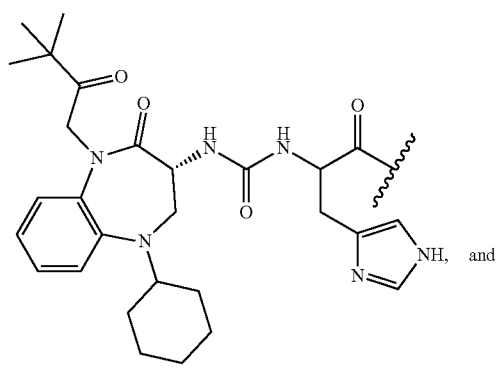

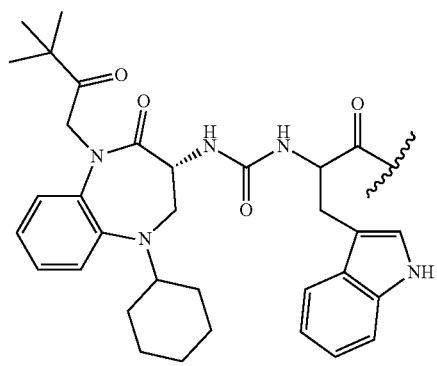 [SMILES: *C(=O)C(Cc1c[nH]c2ccccc12)NC(=O)N[C@@H]1CN(C2CCCCC2)c2ccccc2N(CC(=O)C(C)(C)C)C1=O]

wherein the values of m and n are independently selected from the values 0, 1, or 2, wherein L is a linker selected from the group consisting of glutamic acid,

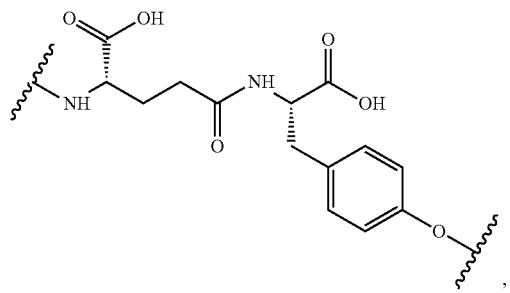

-continued

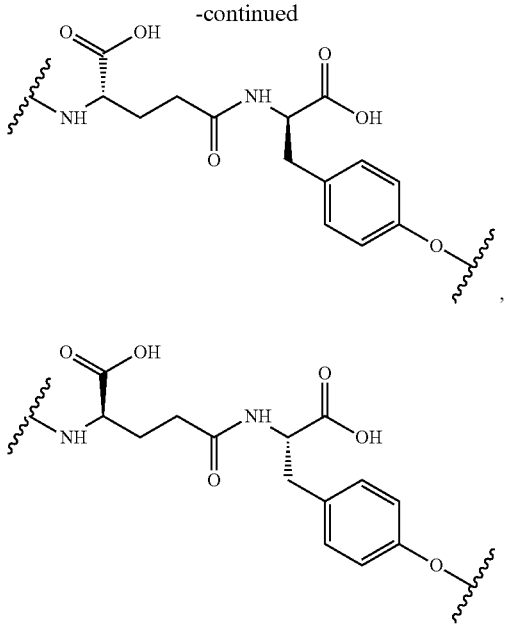

and

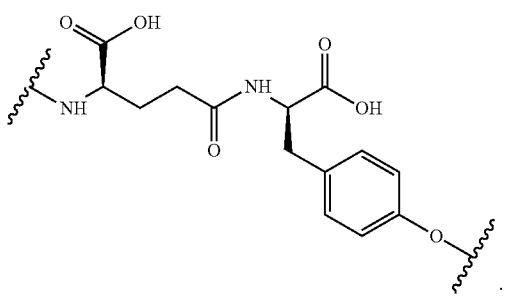

and
wherein Z is an imaging agent represented by the formula:

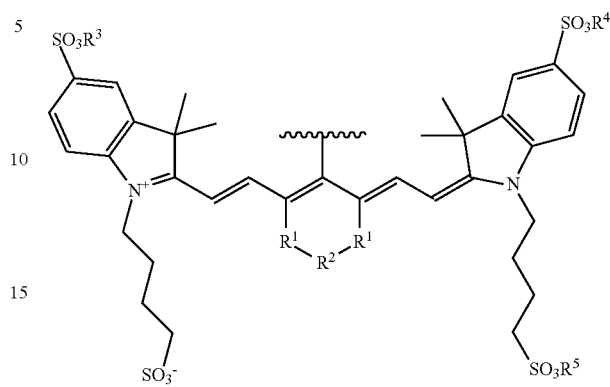

wherein, $R^1$ is independently selected from the group consisting of O, S, N and C, $R^2$ is independently selected from the group consisting of $CH_2$ and $CH_2CH_2$, and each of $R^3$, $R^4$, and $R^5$ are independently selected from the group consisting of H, Na, K, and $NH_4$ or a salt thereof, or isotopes thereof wherein L enhances the binding affinity and biodistribution of the compound.

2. The compound of claim 1 wherein Z has an absorption and emission maxima in the visible spectrum.

3. The compound of claim 1 wherein Z has an absorption and emission maxima of about 680 nm to about 800 nm.

4. The compound of claim 1, wherein the compound is capable of or adapted to fluoresce after distribution thereof in tissue.

5. The compound of claim 1 wherein the compound is adapted to fluoresce by subjecting the compound to excitation light of near infrared wavelength.

6. The compound of claim 1 wherein the compound is highly selective for targeting to a tumor cell.

7. A compound having the formula selected from the group consisting of

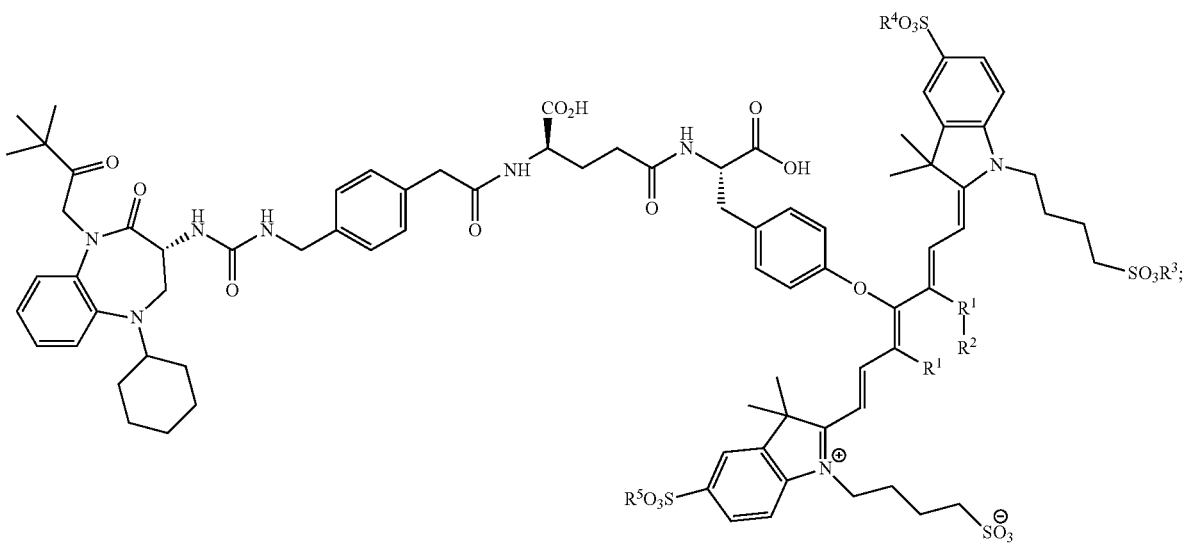

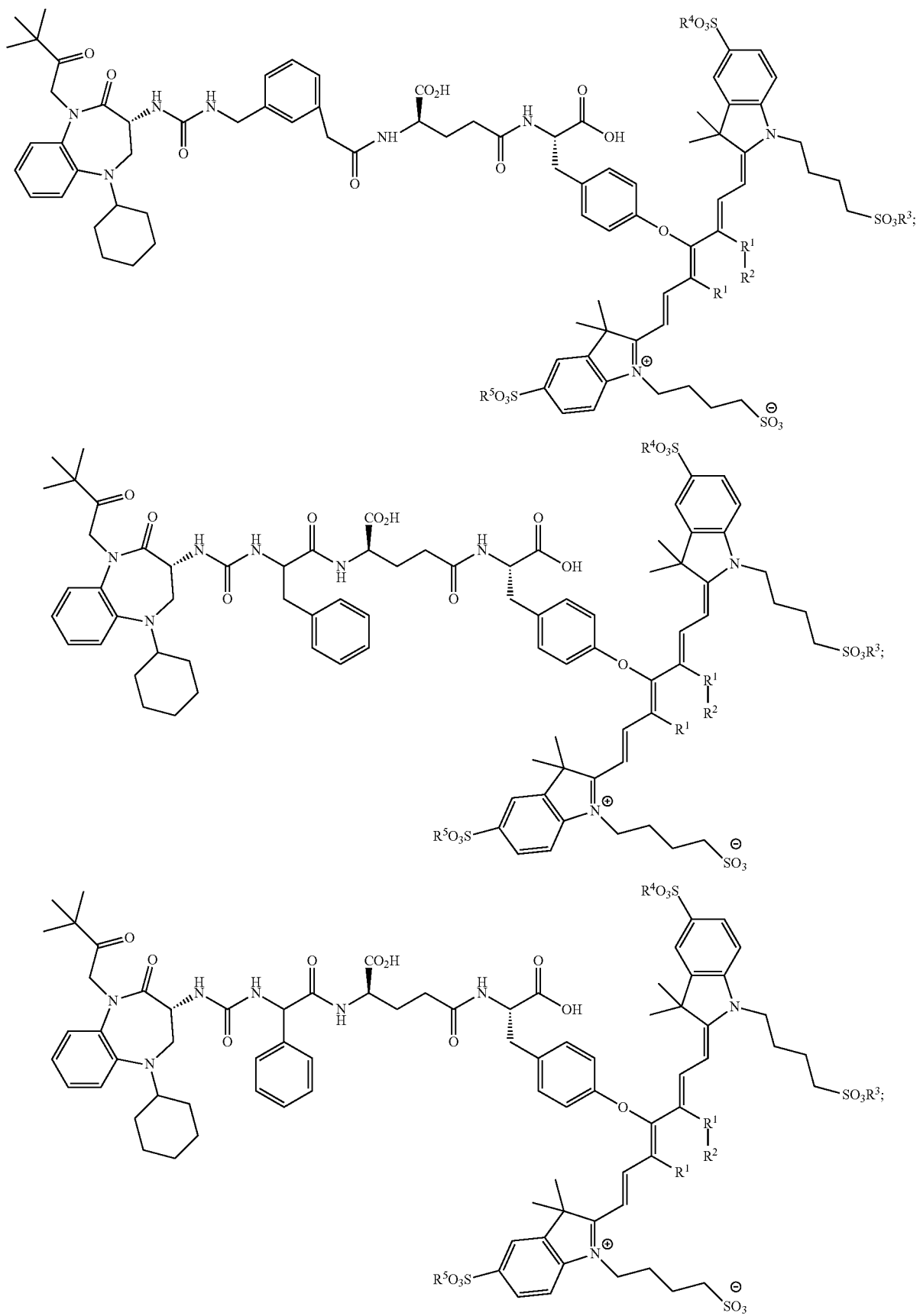

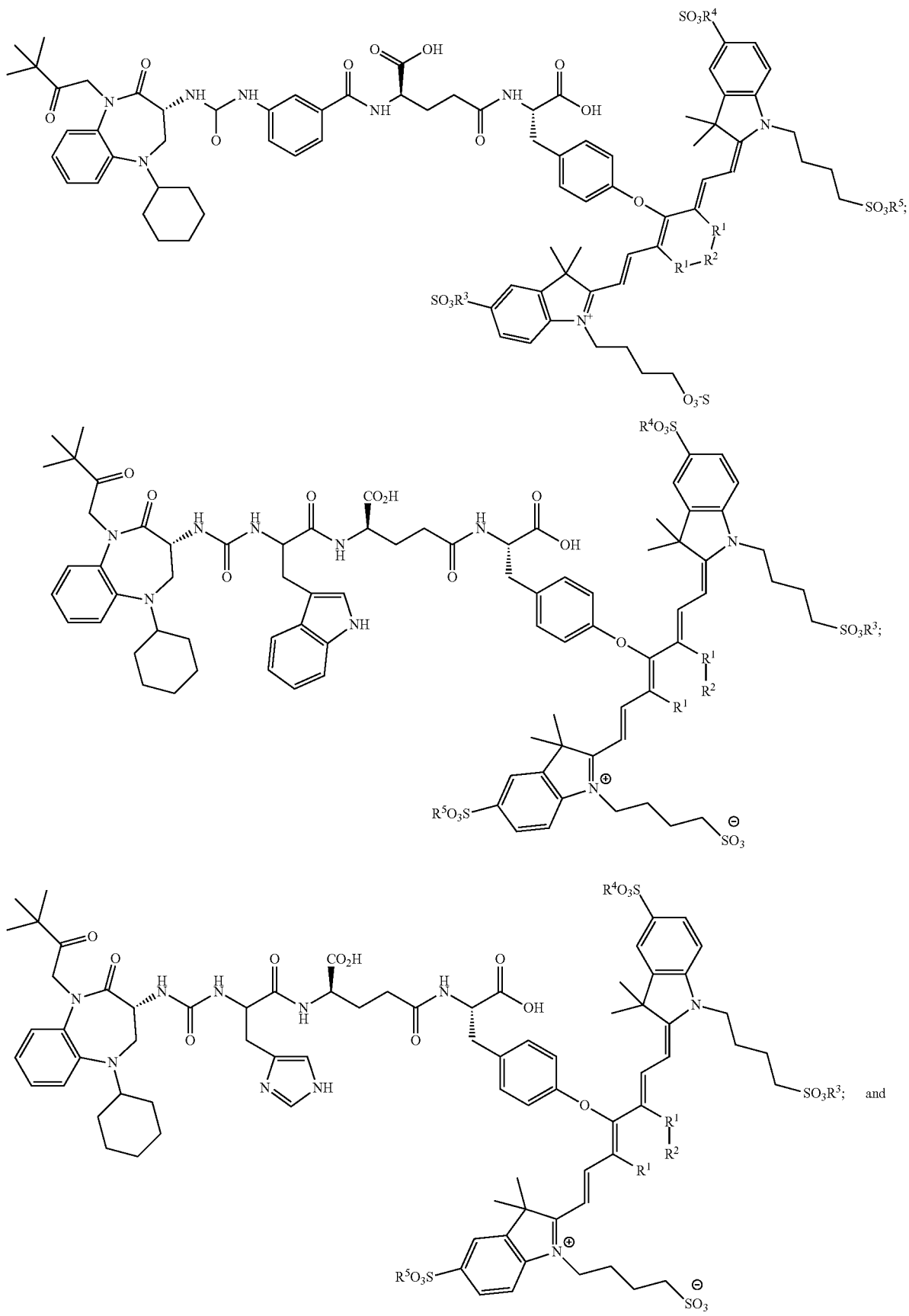

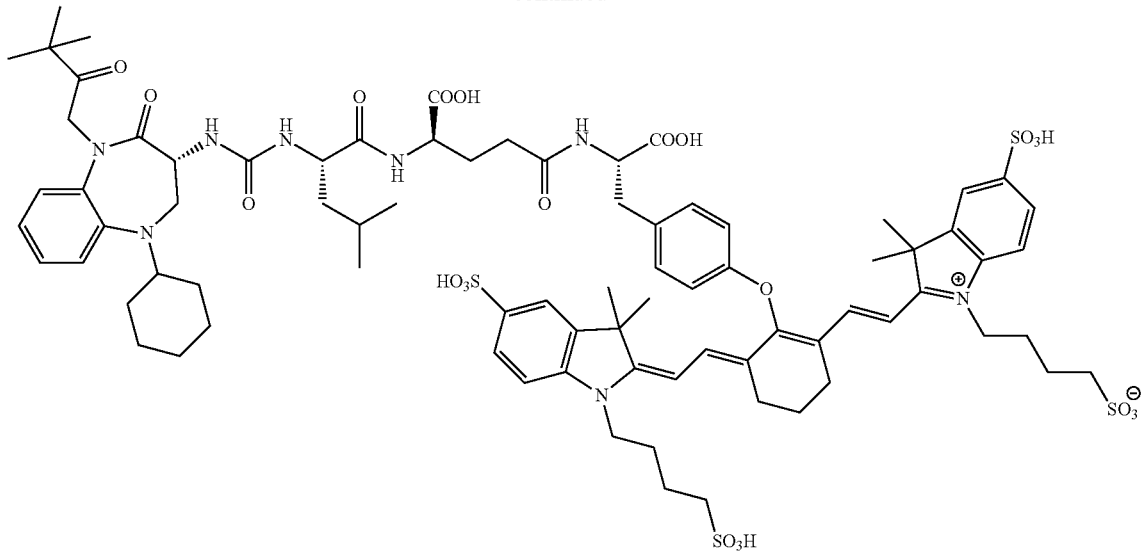

wherein, $R^1$ is independently selected from the group consisting of O, S, N and C, $R^2$ is independently selected from the group consisting of $CH_2$ and $CH_2CH_2$, and each of $R^3$, $R^4$, and $R^5$ are independently selected from the group consisting of H, Na, K, and $NH_4$, or a salt thereof, or isotopes thereof, wherein the compound comprises a targeting ligand capable of selectively binding to CCK2R and/or CCK2i4svR and a linker that enhances the binding affinity and biodistribution of the compound.

8. A composition comprising a compound of claim 1 and a pharmaceutically acceptable carrier, excipient or diluent.

9. A kit comprising a compound of claim 1 and a pharmaceutically acceptable carrier, excipient or diluent.

10. The kit of claim 9, wherein the kit is used for imaging of CCK2 receptor expressing cells.

11. The kit of claim 10, wherein the cells are tumor or cancer cells.

12. The kit of claim 11, wherein the tumor or cancer is selected from the group consisting of kidney cancers, medullary thyroid cancers, insulinomas, small cell lung cancers, bronchial, and ileal carcinoids, GIST tumors, and colon cancers, hepatocellular carcinomas, and pancreatic cancers.

13. The compound of claim 1, wherein the salt is a pharmaceutically acceptable salt.

14. The compound of claim 7, wherein the salt is a pharmaceutically acceptable salt.

* * * * *